United States Patent [19]

Yamazaki et al.

[11] Patent Number: 5,098,417
[45] Date of Patent: Mar. 24, 1992

[54] CELLULOSIC WOUND DRESSING WITH AN ACTIVE AGENT IONICALLY ABSORBED THEREON

[75] Inventors: Hiroshi Yamazaki, Ontario, Canada; Masao Miyazaki, Tokyo, Japan; Kouchi Matsumoto, Ontario, Canada

[73] Assignee: Ricoh Kyosan, Inc., Tokyo, Japan

[21] Appl. No.: 508,178

[22] Filed: Apr. 12, 1990

[51] Int. Cl.$^5$ .............. A61F 13/00; A61L 15/00; A61L 15/16
[52] U.S. Cl. .............. 604/304; 604/375; 604/376; 424/445; 424/446
[58] Field of Search .............. 604/304, 375, 376; 424/445, 446

[56] References Cited

U.S. PATENT DOCUMENTS

| | | | |
|---|---|---|---|
| 2,381,621 | 8/1942 | Schmelkes et al. | 167/84 |
| 2,804,425 | 8/1957 | Smith et al. | 167/84 |
| 3,067,745 | 12/1962 | Burgeni et al. | 604/376 |
| 3,359,258 | 12/1967 | Toms | 260/231 |
| 3,563,241 | 2/1971 | Evans et al. | 604/376 |
| 3,567,358 | 3/1971 | Soignet et al. | 8/116 |
| 3,817,702 | 6/1974 | Paulus et al. | 424/445 |
| 3,889,678 | 6/1975 | Chatterjee et al. | 604/368 |
| 3,910,230 | 10/1975 | Mercer | 118/117 |
| 3,918,899 | 11/1975 | Perrier et al. | 8/120 |
| 3,987,797 | 10/1976 | Stephenson | 128/335 |
| 3,997,647 | 12/1976 | Lassen | 8/120 |
| 4,026,291 | 5/1977 | Nagano et al. | 604/359 |
| 4,242,242 | 12/1980 | Allen | 604/375 |
| 4,340,731 | 7/1982 | Colombo et al. | 604/376 |
| 4,549,011 | 10/1985 | Herzberg et al. | 536/31 |
| 4,585,652 | 4/1986 | Miller et al. | 424/83 |

FOREIGN PATENT DOCUMENTS

| | | | |
|---|---|---|---|
| 0689429 | 1/1967 | Belgium | 604/304 |
| 486203 | 9/1952 | Canada . | |
| 503389 | 6/1954 | Canada . | |
| 547091 | 10/1957 | Canada . | |
| 588169 | 12/1959 | Canada . | |
| 839229 | 4/1970 | Canada . | |
| 1049407 | 2/1979 | Canada . | |
| 2007096 | 5/1979 | United Kingdom . | |

Primary Examiner—Randall L. Green
Assistant Examiner—Paul Prebilic
Attorney, Agent, or Firm—Nixon & Vanderhye

[57] ABSTRACT

A wound dressing is provided herein for systemic administration of a physiologically- or biologically-active agent by controlled release of the agent into such wound. The wound dressing includes a substrate in the form of a fabric or cloth, at least a portion of which is cellulosic, which has been chemically modified to convert hydroxyl groups in the cellulosic portion to ionic-adsorbing sites. An ionic form of a physiologically- or biologically-active agent, namely an antibacterial agent, an antifungal agent, an analgesic agent, a tissue healant agent, a local anesthetic agent, an antibleeding agent, an enzyme or a vasoconstrictor is adsorbed in that substrate. Ionic bonds hold that agent temporarily to the substrate for controlled release therefrom in proportion to the amount of exudate in contact with the substrate. The ionic bonds are formed by adsorbing that agent on that substrate at room temperature. The ionic bonds disassociate upon contact with body exudate from wounds to which the wound dressing is applied by ion exchange with ions in the body exudate, thereby to release that agent in an amount in proportion to the amount of the exudate in contact with the substrate.

42 Claims, 8 Drawing Sheets

CELLULOSIC WOUND DRESSING WITH AN ACTIVE AGENT IONICALLY ABSORBED THEREON

BACKGROUND OF THE INVENTION

(1) Related Inventions

This application is a continuation-in-part of copending and commonly owned application Ser. No. 07/213,920 filed June 30, 1988 now abandoned, the entire contents of which is expressly incorporated herein by reference.

(2) Field of the Invention

This invention relates to ionic forms of dressings to which a variety of ionic, physiologically- and/or biologically- active materials can be adsorbed so that a controlled release of that material into body exudates of wounds can take place. This invention also relates to methods and systems for preparing a derivatized substrate having ionic groups therein for the preparation of such wound or burn dressings.

(3) Description of the Prior Art

When drugs are systemically administered to treat wounds (including cuts, abrasions, incisions, ulcers and infected wounds or burns), a large portion of the drugs is either degraded or adsorbed by nontarget tissues and only a small portion of the initial dose reaches the target site. The efficiency of systemic dosing is further decreased in the trauma patient (as in accidents, earthquakes, fires and wars) who often suffer a decreased vascular flow and thus have reduced drug circulation. Furthermore, the trauma patient often fails to provide information regarding sensitivity to drugs, or fails to take drugs orally. Topical drug administration, in theory, would provide immediate, direct, and sustained effects at the target site, and reduce side-effects and degradation of drugs encountered in systemic dosing. Topical application also permits rapid removal and replacement of drugs when adverse effects are noticed. When cleansing is not readily available, topical application is more effective in destroying microbial spores because a higher concentration of drugs can be applied. Thus, treatment of wounds or burns will benefit from an improvement of topical administration, whether used alone or in conjunction with systemic dosing.

Currently, antibiotics, e.g. fusidic acid, chlorohexidine, Neomycin, Polymyxin and Bacitracin are topically applied in gel, cream or ointment forms (occasionally in aerosol and powder). Because a high concentration of the drugs are in direct contact with the target tissue, some of the drugs cause allergic reaction by contact with the target tissue, some of drugs cause allergic dermatitis, particularly in patients with stasis ulcers or eczema, or exhibit toxicity.

The art is replete with patents involving the more absorption without ionic bonding of drugs on carriers. Thus, Canadian Patent No. 486,203 to Johnson & Johnson taught the use of gauze, as a carrier, Canadian Patent No. 503,389 to Casumano taught the use of gauze pads, as a carrier, and Canadian Patent No. 823,628 to Wyant used paper toweling as a carrier.

Canadian Patent No. 547,091 to Lerner used materials, e.g. aluminum foil, regenerated cellulose sheets or impervious, grease-proof glassine paper, which have non-capillary faces as carriers.

Canadian Patent No. 588,169 to Chicopee used non-woven fabrics, optionally bonded with internally-plasticized polyvinyl acetates.

Canadian Patent No. 839,229 to Astra used sheets of water-soluble, film-forming compounds.

Canadian Patent No. 1,049,407 to Pharmacia used water-insoluble, hydrophilic macromolecular materials.

U.S. Pat. No. 2,381,621 patented Aug. 7, 1945 by Wallace & Teirnan Products, Inc. taught a therapeutic article including a base material comprising a thin, pliable, hydrophilic, non-porous but water-penetrable material in film form and a plurality of water-soluble medicinal substances distributed by being absorbed but not ionically bound to the base material.

U.S. Pat. No. 2,804,425 patented Aug. 27, 1957 by American Cyanamid Company taught a sterile, anhydrous, storage-stable chlortetracycline-containing wound packing comprising a lintless, heavy-metal-free gauze impregnated with, but not ionically-bonded to, chlortetracycline.

U.S. Pat. No. 3,817,702 patented June 18, 1974 by Bayer Aktiengessellschaft taught an antimicrobial textile material comprising a textile material containing reactive hydrogen sites, e.g. cotton treated with a reagent to introduce anion-active sites, which was then chemically reacted with a biocide to form a salt of the biocide with the textile material. The textile material thus became anion-active, and was finished by treatment with a cation-active microbiocide the ionic bond being so strong as to provide a lastingly, partially anion-active textile material.

U.S. Pat. No. 3,987,793 patented Oct. 26, 1976 by Ethicon Inc. provided a surgical suture which was coated with a ionically-bonded, block elastomeric copolymer so that it was receptive to treatment with antimicrobial compounds the bonding between the copolymer and the antimicrobial compound being so strong as to produce a substance having long-lasting antimicrobial properties.

U.S. Pat. No. 4,549,011 patented Oct. 22, 1985 by Orgenics Ltd. provided a sheet of cellulose or plastic material which was activated with a compound which can covalently bind a liquid thereto, and then a ligand is then coated on the sheet. The ligand is one having an affinity for a substance to be separated from a mixture of substances.

U.S. Pat. No. 4,585,652 patented Apr. 29, 1986 by Regents of the University of Minnesota provided a controlled drug release system comprising a polymer which, in its ionic state, was loaded with bioactive counterions. When the polymer was neutralized the counterions were released into the surrounding medium. The patentee used an electrode comprising a polymer which changed its ionic state for loading and for discharging purposes. This was an unnecessarily complicated system and did not have practicability for general use.

U.K. Patent Application GB 2007096 A published 16th of May, 1979 provided an indicator to show when an antimicrobial composition, which was impregnated in, but not ionically bonded to, a cloth was no longer present in the cloth. The antimicrobial composition was ionically-bonded to a dye, so that when the antimicrobial composition was exhausted from the cloth, the dye also was exhausted, and so no color remained.

To provide a controlled release of drugs, a U.S. Army medical team had developed microcapsules (diameters of <10 μ) containing ampicillin for topical application to wound sites. However, these delivery systems (gel, cream, ointment, powder and microcapsule) suffer a practical problem: their even application or removal to and from the target site requires gentle manipulation and is too time-consuming for treatment of a large number of trauma patients in emergency cases.

To overcome this problem, gauze dressings impregnated with a suspension of antibiotics (e.g., fusidic acid and Neomycin) in appropriate media (e.g., petroleum jelly and lanolin) had also been developed. However, such delivery system did not control the release of drugs and thus did not solve the allergy or toxicity problems. Furthermore, the dressings impregnated with gel or liquid did not adsorb the exudate, and may not have provided sufficient breathability which would be desired for the treatment.

Enzymes, e.g. fibrinolytic proteases and deoxyribonucleases, have occasionally been used to dissolve fibrous or purulent accumulations in infected wounds or burns. These enzymes are currently applied in the form of gels (e.g., carboxymethyl cellulose gel) or ointments. Such systems would suffer the same problems of allergy and time-consuming application described above. Furthermore, they did not provide mechanisms for removal of enzymic hydrolysates which are potential irritants.

Apparatus for the treatment of textiles with aqueous solutions of treating agents are also well-known in the art. For example, U.S. Pat. No. 3,910,230, patented Oct. 7, 1975, by H. L. Mercer, provided an apparatus for applying a desired percentage by weight of liquid to a running textile fabric.

U.S. Pat. No. 2,426,668, patented Jan. 27, 1981, by W. Spillmann et al, provided apparatus and methods for the treatment of a web or a number of webs of material guided side by side in the nip between treatment rollers, the web or webs of material being impregnated with or containing treating agents.

U.S. Pat. No. 3,817,702, patented June 18, 1974, by Bayer Aktiengesellschaft provide a laboratory-scale procedure for preparing textile materials lastingly protected from staining by damp and mildew and from rotting by a cation-active microbial. The process taught involved impregnated the fabric, squeezing off the excess, and then drying the fabric. The cation-active microbial was then absorbed by the fabric from an aqueous solution. The excess was squeezed off and unfixed portions of the active compound was washed away.

Some currently-available, commercially-usable processes for the preparation of diethylaminoethyl cellulose (DEAE) and carboxymethyl cellulose (CM) derivatives are directed to modifying fibres or beads of polyhydroxy polymers and often require stirring and heating for relatively long periods of time. For example, U.S. Pat. No. 3,359,258, patented Dec. 19, 1967, by B. A. Toms, provided a commercially-usable process for preparing DEAE by first reacting alkali cellulose and aminoethyl hydrogen sulphate to form aminoethyl cellulose and then further reacting this product with dimethyl sulphate in the presence of an acid binder. In the process taught, a sheet of pulp was impregnated with aminoethyl hydrogen sulfate in a tray. The damp sheet was removed from the tray and then heated, either intact or after shredding. The impregnated pulp, whether in the form of sheet or crumb, was dried and baked under controlled conditions, e.g., at a temperature of about 105° C., for about 2–4 hours. The so-dried sheet or crumb was then coarsely crumbled and dried in air at about 110° C.

Other currently available commercially-usable processes have been developed which involved treating cellulose fabrics in the same way. For example, U.S. Pat. No. 3,567,358, patented Mar. 2, 1971, by D. M. Soignet et al, provided cellulose fabrics which were diethylaminoethylated and/or carboxymethylated and thereafter were heated at elevated temperatures under vacuum for extended periods of time to form crosslinks.

U.S. Pat. No. 3,918,899, patented Nov. 11, 1975, by D. M. Perrier et al, provided, as textiles, CM-celluloses, e.g., CM-cottons, prepared in aqueous media.

U.S. Pat. No. 3,997,647, patented Dec. 14, 1976, by F. O. Lassen, provided filaments of chemically-modified cellulose fibres and webs constructed from such filaments.

The synthesis and characterization of DEAE and CM derivatives of polysaccharides, e.g. cellulose, dextran and starch, are well-documented. The derivatives are non-toxic, non-allergenic and have been used as food additives or pharmaceuticals. Although these derivatives are provided in fiber, powder or granular forms, cloth forms of the derivatives are not commercially available. The cloth forms have definite advantages in large-scale purification and immobilization of ionic macromolecules (e.g., enzymes) because they provide easy handling (washing, transfer and removal) and faster flow in a packed bed operation. High degrees of derivatization of the cotton cloth tend either to stiffen the fabric texture, or to reduce the fabric strength. Furthermore, the edges of the woven fabric tend to ravel after modification. Cotton surgical dressing or gauze suffer even greater textural changes.

Currently available methods for DEAE and CM derivatization are aimed for modifying fibers or beads of polyhydroxy polymers and often require stirring and heating for relatively short periods of time. Since efficient stirring and rapid heating are difficult for modification of these fabrics in large sizes and quantities, processes have been devised by the present applicants as will be more fully described hereinafter which allow modification without stirring and at near ambient temperatures.

SUMMARY OF THE INVENTION

Aims of the Invention

Since efficient stirring and rapid heating using the methods and apparatus of the prior art are difficult for the modification of these cloths or fabrics in large sizes and quantities, i.e., on a commercial scale, it is desirable, and accordingly it is an object of this invention, to devise commercially-viable methods and systems which allow such modification without stirring and at near ambient temperatures.

It is another object of this invention to provide ionic forms of dressings which can adsorb physiologically- or biologically-active compounds by ionic bonding, the ionic bond being such the compounds could be released, in a controlled manner, to carry out their biological or physiological activity.

Another object of this invention is to provide commercially-viable methods for the preparation of fabrics having ionic-absorbing sites thereon for use in the preparation of such ionic forms of dressings.

Yet another object of this invention is to provide commercially-viable system for the preparation of fabrics having ionic-absorbing sites thereon for use in the preparation of such ionic forms of dressings.

Statement of Invention

This invention provides a wound dressing for systemic administration of a physiologically- or biologically-active agent by controlled release of such agent into such wound, the wound dressing comprising: (a) a substrate in the form of a fabric or cloth, at least a portion of which is cellulosic, which has been chemically modified to convert hydroxyl groups in the cellulosic portion to ionic-adsorbing sites; (b) an ionic form of a physiologically- or biologically-active agent adsorbed in the substrate, that agent being selected from the group consisting of antibacterial agents, antifungal agents, analgesic agents, tissue healant agents, local anesthetic agents, antibleeding agents, enzymes and vasoconstrictors; and (c) ionic bonds holding that agent temporarily to the substrate for controlled release therefrom in proportion to the amount of exudate in contact with the substrate, the ionic bonds being formed by adsorbing the agent on the substrate at room temperature, the ionic bonds disassociating upon contact with body exudate from wounds to which the wound dressing is applied by ion exchange with ions in the body exudate, thereby to release the physiologically- or biologically-active agent in an amount in proportion to the amount of the exudate in contact with the substrate.

This invention also provides a process for preparing such wound dressings, which comprises chemically modifying a substrate, at least a part of which is cellulosic to form ionic-adsorbing sites thereon; and soaking the chemically-modified substrate in an aqueous, or aqueous alcoholic, solution of a physiologically- or biologically-active agent to be adsorbed therein and to be held therein and thereon; whereby, upon contact with body exudate from wounds to which such wound dressing is applied, the physiologically- or biologically-active agent is released in a controlled manner by ion exchange with the ions in the body exudate in proportion to the amount of exudate.

This invention also provides a derivatized substrate, at least part of which is cellulose, such derivatized substrate being chemically modified to have ionic-adsorbing sites thereon, preferably of the dialkylamino, carboxyalkyl or sulfate type, the ionic groups being such that the strength of an ionic bond between the ionic groups and an ionic form of an active agent permits the active agent to be released by an ion exchange with ions in an eluate in proportion to the amount of the eluate.

This invention also provides a process for preparing such derivatized substrate which comprises chemically modifying a substrate, at least a part of which is cellulosic, to form ionic-adsorbing sites thereon of the ionic-absorbing sites being such that the strength of an ionic bond between the ionic-absorbing sites and an ionic form of an active agent permits the active agent to be released in controlled manner by ion exchange with ions in an eluate in proportion to the amount of eluate.

This invention also provides a method for preparing a derivatized substrate, at least part of which is cellulosic, the substrate having ionic groups therein, by reaction with at least one chemical reactant solution including the steps of soaking the substrate by passing the substrate through a bath of an appropriate chemical reactant solution, and squeezing the excess solution from the soaked substrate to provide a wetted substrate, the method comprising the additional steps of: supporting the wetted substrate on a suitable backing member which substantially inhibits the escape of the solution from the environment of the wetted substrate; curing the so-supported substrate in a heating zone to provide the derivatized substrate; washing the derivatized substrate; and suitably drying the washed derivatized substrate.

The present invention also provides a system for preparing the above-defined derivatized substrate including a container provided with means for guiding the substrate downwardly to near the bottom thereof, then laterally near the bottom thereof, and then upwardly out of the container whereby, when the container contains an appropriate chemical reactant solution, the passing of the substrate through the bath of the appropriate chemical reactant solution, substantially soaks the substrate with the solution, and roller means between which the substrate is adapted to be fed, thereby squeezing excess solution from the saturated substrate to provide a wetted substrate. The improved such system includes: supporting means operatively coupled to curing means for drying and curing the substrate while the substrate is supported on a suitable backing which substantially inhibits the escape of such solution or solutions from the environment of the wetted substrate; washer means for washing the cured substrate; and means for drying the washed cloth.

Other Features of the Invention

The substrate to be treated by the method of the present invention may be any suitable non-woven, woven, knitted, netted or knotted fabric containing at least some reactive cellulose or reactive hydrogen-group containing material. This fabric may contain at least some yarns formed from a mixture of fibres of organic derivatives of cellulose and other fibres. Any suitable organic derivative of cellulose, e.g., as the organic esters of cellulose and cellulose ethers may be employed for forming the fibres. Examples of organic esters of cellulose are cellulose acetate, cellulose formate, cellulose propionate and cellulose butyrate, while examples of cellulose ethers are ethyl cellulose, methyl cellulose and benzyl cellulose.

The fabrics may contain, in addition to the yarns comprising organic derivatives of cellulose fibres, other yarns, e.g., yarns formed from substantially continuous filaments of reconstituted or regenerated cellulose or organic derivatives of cellulose. Fabrics may also be formed by interweaving yarns containing organic derivative of cellulose fibres with yarns formed of cotton fibres or mixtures of the same.

The artificial fibres employed in forming at least some of the yarns in the fabric may be made by any suitable method. A plurality of filaments as they are formed, or from a plurality of preformed packages, may be grouped together in the form of a rope or they may be formed into a band, then cut or torn to suitable lengths.

The substrate at least part of which is cellulosic, may be a fabric, for example, a non-woven fabric, i.e., a non-woven rayon fabric, or a non-woven rayon/polyester fabric; and may be either in its open apertured form or in its highly absorbent, open-apertured form.

For topical application, pliability, softness and low linting of dressings are desired. It has been found by the present applicants that modification of nonwoven cellulose-polyester blend fabrics produces suitable substrates for ionic dressings. Unmodified, nonwoven cellulose fabrics are commercially available. For example, rayon/polyester non-woven fabric blends (known by the Trade Marks SONTARA 8423 and SONTARA 8407) may be used. These substrates are free of chemical additives (e.g. resins), binder and finish (which would interfere with modification); are soft, pliable and low linting; and have nonravelling edges and good adsorbency. Some additional features of SONTARA are: drapeable; high bulk at low weight; outstanding conformability; good wet and dry strength per unit of weight; flame resistance; excellent cover and uniformity; will not delaminate. Because of the polyester part, the fabric strength is less affected by modification than 100% cellulose fabrics. While SONTARA is produced in four basic product types with a variety of styles available, only those at least a part of which is cellulosic may be used as substrates in the present invention. The apertured style (known by the Trade Mark SONTARA 8407) has been used as medical dressing, because of greater breathability.

SONTARA is the registered trademark of DuPont for its spin-laced fabrics. SONTARA is a bulky, soft, strong, conformable, lightweight sheet made of hydraulically interlaced fibers with no chemical or thermal bonding. Nonwoven structures offer greater flexibility than conventional fabrics, films, or paper. Some typical properties of SONTARA as shown in the following table:

preferably selected from the group consisting of: an antibacterial selected from the group consisting of fusidic acid, pseudomonic acid, Ceftriaxone (Rocephin); an antifungal selected from the group consisting of nafcillin, Nystatin, and undecylenic acid; an analgesic selected from the group consisting of salicylic acid, salicylsulfonic acid and nicotinic acid; and an antibleeding agent selected from the group including adenosine diphosphate, such antibleeding agents being such that they make platelets sticky, an initial step required for the stopping of bleeding. Such physiologically- or biologically- active agents may be used in the form of their salts.

Further specification of some of the above-described anionic drugs are as follows:

1. Fusidic Acid is also known as (Z)-16 -(Acetyloxy)-$3\alpha,11\alpha$- dihydroxy-29-nor-$8\alpha,9$ ,$13\alpha$, 14-dammara-17(20),24-dien-21-oic acid; $3\alpha,11\alpha,16\gamma$-trihydroxy-29-nor-$8\alpha,9$ ,$13\alpha,14$ -dammara-17(20),24-dien-21-oic acid 16-acetate; $3\alpha,11\alpha,16$ -trihydroxy-$4\alpha,8,14$-trimethyl-18-nor-$5\alpha,8\alpha,9$ ,$13\alpha,14\gamma$-cholesta-17(20),24-dien-21-oic acid 16-acetate; 3,11,16-trihydroxy-4,8,10,14-tetramethyl-17-(1'-carboxyisohept-4'-enylidene)cyclo-pentanoperhydrophenanthrene 16-acetate; and ramycin. Its sodium salt, sodium fusidate, is also known as ZN 6, Fucidine, Fucidina, Fucidine and Fucidin Intertulle.

2. Pseudomonic Acids. A group of antibacterial antibiotics produced by Pseudomonas fluorescens NCIB 10586 that have unusual structural features. Four mem-

| | TYPICAL PHYSICAL PROPERTIES OF SONTARA (SI Units) | | | | | | | | | |
|---|---|---|---|---|---|---|---|---|---|---|
| | | | SHEET GRAB TENSILE (N) | | TRAPE- ZOID TEAR (N) | | MULLEN | FRAZIER AIR PERMEABILITY | ROLL SIZE (17.8 cm ID CORE) | |
| Style | UNIT WEIGHT ($g/m^2$) | THICKNESS (mm) | MD | XD | MD | XD | BURST (kPa) | ($m^3/m^2 \cdot S$) @ 124 Pa) | cm O.D. | lin. meters |
| 70/30 Rayon/ Polyester Blends | | | | | | | | | | |
| 8407 (apertured style) | 51 | .41 | 49 | 36 | 22 | 31 | 140 | 4.0 | 110 | 2400 |
| 8423 | 78 | .66 | 58 | 67 | 18 | 22 | 165 | 1.3 | 110 | 2400 |
| ASTM Test Method | D1117 Sec. 17 | D1117 Sec. 19 | D1117 Sec. 7 | | D1117 Sec. 14 | | D1117 Sec. 8 | D1117 Sec. 6 | | |

The cloth substrate may be a dialkylaminoalkyl cloth, e.g., a diethylaminoethyl, a diethylaminopropyl, a diethylaminomethyl, a dimethylaminoethyl or a dimethylaminopropyl cloth; or it may be a carboxyalkyl cloth, e.g., a carboxymethyl, a carboxyethyl or a carboxypropyl cloth; or it may be a sulfate cloth. The diethylaminoethyl, the carboxyethyl or the sulfate cloths are preferable.

The physiologically- or biologically- active agent may be an antibacterial agent, an antifungal agent, an analgesic agent, a tissue healant agent, a local anesthetic agent, an antibleeding agent, an enzyme or a vasoconstrictor. Such agents may be used in the form of their salts.

Where the substrate is in dialkylaminoalkyl form, i.e. a cloth having anionic-adsorbing sites, the physiologically- or biologically- active agent is an anionic drug, bers of the group are known: pseudomonic acid A, the major component, pseudomonic acid B, the 3,4,5-trihydroxy analog of A (also referred to as pseudomonic acid I), pseudomonic acid D, the 4-nonenoic acid analog of A; and pseudomonic acid C, in which the epoxide oxygen is replaced by a double bond.

Pseudomonic Acid A. Mupirocin. [2S-[$2\alpha(E),3\beta,4\beta,5\alpha$[2R*,3R*-((1R*,-2R*)]]]-9-[[3-Methyl-1-oxo-4-[tetrahydro-3,4-dihydroxy-5-[[3-(2-hydroxy-1-methylpropyl)oxiranyl]methyl]-2H-pyran-2-yl]-2-butenyl]oxy]nonanoic acid; pseudomonic acid A; trans-pseudomonic acid; BRL-4910A; Bactoderm; Bactroban; Eismycin. $C_{26}H_{44}O_9$; mol wt 500.63. C 62.38%, H 8.86%, O 28.76%. Major component of the pseudomonic acids, q.v., an antibiotic complex produced by Pseudomonas fluorescens NCIB 10586.

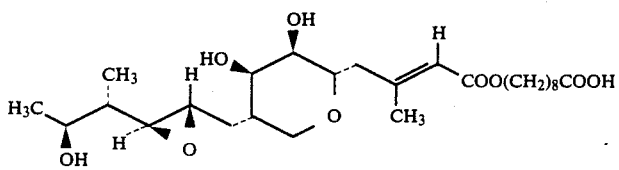

Pseudomonic Acid C, $C_{26}H_{44}O_8$, [2S-[2α(E),3β,4β,5α(2E,4S*,5R*)]]-9-[[3-methyl-1-oxo-4-tetrahydro-3,4-dihydroxy-5-(5-hydroxy-4-methyl-2-hexenyl)-2H-pyran-2-yl]-2-butenyloxy)nonanoic acid.

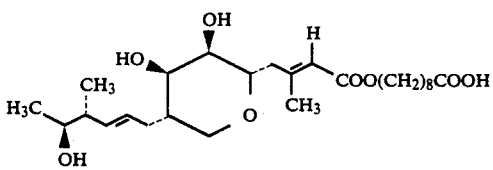

Pseudomonic acid D, $C_{26}H_{42}O_9$, [2S-[2α[E(E)],3β,-4β,5α-[2R*,3R*(1R*,2R*)]]-9-[[3-methyl-1-oxo-4-Tetrahydro-3,4-dihydroxy-5-[[3-(2-hydroxy-1-methylpropyl)oxiranyl]-methyl]-2H-pyran-2-yl)-2-butenyl]oxy)-4-nonenoic acid.

3. Nafcillin is also known as 6-(2-Ethoxy-1-naphthamido)-3,3-dimethyl-7-oxo-4-thia-1-azabicyclo[3.2.0-]heptane-2-carboxylic acid; 6-(2-ethoxy-1-naphthamido)penicillanate; and 6-(2-ethoxy-1-naphthamido)penicillin. The sodium salt is also known as Naftopen and Unipen.

4. Nystatin is also known as Fungicidin; Diastatin; CandioHermal; Mycostatin; Moronal; Nystan; Nystavescent; and O-V Statin.

5. Undecylenic Acid, also known as 10-Undecenoic acid; 10-hendecenoic acid; 9-undecylenic acid; Declid; Renselin; and Sevinon.

6. Salicylic Acid is also known as 2-Hydroxybenzoic acid.

7. Salicylsulfuric Acid is also known as 2-(Sulfooxy)-benzoic acid; salicylic acid, acid sulfate; and salicylic acid sulfuric acid ester.

8. Nicotinic Acid is also known as 3-Pyridinecarboxylic acid; pyridine-γ-carboxylic acid; P.P. factor; pellagra preventive factor; antipellagra vitamin; niacin; Nicacid; Nicagin; Niconacid; Nicotinipca; Nicyl; Akotin; Daskil; Tinic; Nicolar; and Wampocap.

9. Adenosine Diphosphate is also known as Adenosine 5'-(trihydrogen diphosphate); ADP; adenosine 5'-pyrophosphoric acid; 5'-adenylphosphoric acid; and adenosinediphosphoric acid.

Where the substrate is a cloth having cationic-adsorbing sites, e.g., a carboxyalkyl-cloth or a $SO_3$-cloth, the physiologically- or biologically- active agent is a cationic drug, preferably selected from the group consisting of: an anti-bacterial selected from the group consisting of chlorhexidine, Bacitracin, Chlortetracycline, Gentamycin, Kanamycin, Neomycin B, Polymyxin B, Streptomycin, and Tetracycline; an antifungal selected from the group consisting of Amphotericin B, Clotrimazole, and Miconazole; tissue healants selected from the group consisting of cysteine, glycine and threonine; local anesthetics, e.g., Lidocaine; enzymes selected from the group consisting of trypsin, Streptokinase, plasmin (Fibrinolysin) and Streptodornase; deoxyribonuclease; and a cationic vasoconstrictor selected from the group consisting of epinephrine and serotonin. Such physiologically- or biologically- active agents may be used in the form of their salts.

Further specification of some of the above-described cationic drugs are as follows:

1. Chlorhexidine is also known as N,N'''-Bis(4-chlorophenyl)-3,12-diimino-2,4,11,13-tetraazatetradecanediimidamide; 1,1'-hexamethylenlenebis[5-(p-chlorophenyl)biguanide]; 1,6-bis[N'-(p-chlorophenyl)-$N^5$-biguanido]hexane; 1,6-bis($N^5$-p-chlorophenyl-N'-diguanido)hexane; 1,6-di(4'-chlorophenyldiguanido)-hexane; 10,040; Hibitane; Nolvasan; Rotersept; and Sterilon. Its gluconate is known as Hibiscrob.

2. Bacitracin is also known as Ayfivin; Penitracin; Zutracin; and Topitracin.

3. Chlortetracycline is also known as 7-Chloro-4-dimethylamino-1,4,4a,5,5a,6,11,12a-octahydro-3,6,10,12,12a-pentahydroxy-6-methyl-1,11,-dioxo-2-naphthacene carboxamide; 7-chlorotetracycline; Acronize; Aureocina; Aureomycin; Biomitsin; Biomycin; and Chrysomykine.

4. Gentamycin includes Gentamicin $C_{18}$, which is also known as 0-3-Deoxy-4-C-methyl-3-(methylamino)-γ-L-arabinopyranosyl(1→6)-0[2,6-dramino-2,3,4,6-tetradeoxy-α-D-erythro-hexo pyranosy 1-(1→4)]-2-deoxy-D-streptamine and as gentamicin D.

Gentamicin A is also known as O-2-Amino-2-deoxy-α-D-glucopyranosyl-(1→4)-O-[3-deoxy-3-(methylamino)-α-D-xylopyranosyl(1→6)]-2-deoxy-D-streptamine.

The C complex sulfate is also known as Cidomycin, Garamycin, Garasol, Gentalyn, Genticin, Gentocin, Refobacin, and Sulmycin.

5. Kanamycin includes: Kanamycin A sulfate, also known as Cantrex, Cristalomicina, Kamycin, Kamynex, Kanacedin, Kanamytrex, Kanasig, Kanicin, Kannasyn, Kantrex, Kantrox, Otokalixin, Resistomycin (Bayer), Opthalmokalixan, Kantrexil, Kano, Kanescin, and Kanaqua; Kanamycin B, is also known as NK 1006, bekanamycin, and aminodeoxykanamycin; and Kanamycin B sulfate, also known as Kanendomycin, and Kanamycin.

6. Neomycin is also known as Mycifradin; Myacyne; Fradiomycin; Neomin; Neolate; Neomas; Nivemycin; and Vonamycin Powder V. It also includes Neamine, which includes: Neomycin A, and Neomycin B, which is also known as Framycetin, Enterfram, Framygen, soframycin, Actilin, and antibiotique E.F.185. Neomycin B sulfate is also known as Fraquinol, Myacine, Neosulf, Neomix, Neobrettin, and Tuttomycin.

7. Polymyxin, having the structural formula

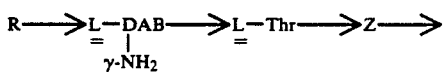

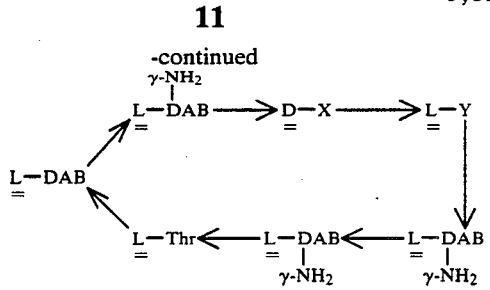

(where DAB=α,γ-diaminobutyric acid) includes:

Polymyxin B, which is a mixture of polymyxins $B_1$ and $B_2$;

Polymyxin B sulfate, which is also known as Aerosporin;

Polymyxin $B_1$, where, in the above Formula, R=(+)-6-methyloctanoyl, X=phenylalanine, Y=leucine, and Z=L-DAB;

Polymyxin $B_1$ hydrochloride;

Polymyxin $B_2$, where, in the above Formula R=6-methylheptanoyl, X=phenylalanine, Y=leucine, and Z=L-DAB;

Polymyxin $D_1$, where, in the above Formula R=(+)-6-methyloctanoyl, X=leucine, Y=threonine, and Z=D-serine;

Polymyxin $D_2$, where, in the above Formula R=6-methylheptanoyl, X=leucine, Y=threonine, and Z=D-serine; and Polymyxin E, which is also known as Colistin. Colimycin; Coly-Mycin; Totazina; and Colisticina.

8. Streptomycin is also known as O-2-Deoxy-2-(methylamino)-α-L-glucopyranoxyl-(1→2)-O-5-deoxy-3-C-formyl-α-L-lyxofurano-syl(→4)-N,N'-bis-(aminoiminomethyl)-D-streptamine; and streptomycin A. Its sesquisulfate is also known as streptomycin sulfate, Agristrep, Streptobrettin, Streptorex, and Vetstrep. Streptomycin B is also known as Mannosidostreptomycin; and mannosylstreptomycin.

9. Tetracycline is also known as 4-(Dimethylamino)-1,4-4a,5,5a,6,-11,12a-octahydro-3,6,10,12,12a-pentahydroxy-6-methyl-1,-11-dioxo-2-naphthacenecarboxamide; deschlorobiomycin; tsiklomitsin; Abricycline; Achromycin; Agromicina; Ambramicina; Ambramycin; Bio-Tetra; Bristaciclina; Cefracycline suspension; Criseo-ciclina; Cyclomycin; Democracin; Hostacyclin; Omegamycin; Panmycin; Polycycline; Purocyclina; Sanclomycine; Steclin; Tetrabon; Tetracyn; Tetradecin. Its hydrochloride is also known as Achro, Achromycin V, Ala Tet, Ambracyn, Artomycin, Cefracycline tablets, Cyclopar, Diacycline, Dumocyclin, Fermentmycin, Mephacyclin, Partrex, Quadracycline, Quatrex, Ricycline, Rocyc-line, Stilciclina, Subamycin, Sustamycin, Teline, Telotrex, Tetra-bid, Tetrachel, Tetracompren, Tetra-D, Tetrakap, Tetralution, Tetramavan, Tetramycin, Tetrosol, Totomycin, Triphacyclin, Unicin, and Unimycin. Its phosphate complex is also known as Panmycin Phosphate, Sumycin, Tetradecin Novum, Tetrex, and Upcyclin. Its lauryl sulfate is known as Lauracycline.

10. Amphotericin B is also known as Fungizone; Fungilin; and Ampho-Moronal.

11. Clotrimazole is also known as 1-(2-Chlorophenyl)diphenyl-methyl]-1H-imidazole; 1-(o-chloro-α,α-diphenylbenzyl)imidazole; 1-[α-(2-chlorophenyl)-benzldryl)imidazole; 1-[(o-chlorophenyl)diphenylmethylimidazole; dipheny-(2-chlorophenyl)-1-imidazolylmethane; 1-(o-chlorotrityl)imidazole; FB 5097; BAY b 5097; and Canesten; Lotrimin; Mycosporin.

12. Miconazole is also known as 1-[2-(2,4-Dichlorophenyl)-2-[(2,4-dichlorophenyl)methoxyethyl]-1H-imidazole; and 1-[2,4-dichloro-γ-[(2,4-dichlorobenzyloxy]phenethyl]imidazole. Its nitrate is also known as R-14889, Albistat, Brentan, Conofite, Daktarin, Dermonistat, Epi-Monistat, Gyno-Daktarin, Gyno-Monistat, Micatin, and Monistat.

13. Cysteine, Cys (IUPAC abbrev.) is also known as OL-cysteine; γ-mercaptoalanine; 2-amino-3-mercaptopropanoic acid; 2-amino-3-mercaptopropionic acid; and α-amino- -thiolpropionic acid.

14. Glycine, Gly (IUPAAC abbrev.), is also known as aminoacetic acid; aminoethanoic acid; glycocoll; and Glycosthene.

15. Threonine, Thr (IUPAC abbrev.), is also known as 2-amino-3-hydroxybutyric acid; α-amino-γ-hydroxybutyric acid; and 2-amino-3-hydroxybutanoic acid.

16. Lidocaine is also known as 2-(Diethylamino)-N-(2,6-dimethylphenyl)acetamide; 2-diethylamino-2',6'-acetoxylidide; α-diethylamino-2,6-dimethylacetanilide; lignocaine; Xylocaine; Xylotox; Leostesin; Rucaina; Isicaine; Duncaine; Xylestesin; Anestacon; Gravocain; Lidothesin; and Xylocitin.

17. Fibronolysin is also known as Plasmin; serum tryptase; Actase; and Thrombolysin.

18. Epinephrine is also known as 4-[1-Hydroxy-2-(methylamino)-ethyl]-1,2-benzenediol; 3,4-dihydroxy-α-[(methylamino)methyl]-benzyl alcohol; 1-(3,4-dihydroxyphenyl)-2-(methylamino)ethanol; 3,4-dihydroxy-1-[1-hydroxy-2-(methylamino)-ethylbenzene; methylaminoethanolcatechol; and adrenalin.

19. Serotonin is also known as 3-(2-aminoethyl)-1H-indol-5-ol; 5-hydroxytryptamine; 3-(γ-aminoethyl)-5-hydroxyindole; 5-hydroxy-3-(γ-aminoethyl)indole; enteramine; thrombocytin; thrombotonin; and 5-HT.

In one embodiment of the process of this invention, the substrate is a non-woven cloth chemically-modified to form anionic-adsorbing sites therein, e.g., dialkylaminoethyl sites, preferably diethylaminomethyl, diethylaminoethyl, diethylaminopropyl, dimethylaminomethyl, dimethylaminoethyl or dimethylaminopropyl sites. The chemical modification may be effected by reaction with diethylaminoethyl chloride hydrochloride and sodium hydroxide containing sodium sulfate, applied separately and sequentially in any order, thereby to provide diethylaminoethyl sites.

In another embodiment of the process of this invention, the substrate is a non-woven cloth chemically-modified to form cationic-adsorbing sites therein. In one variant thereof, these sites are carboxyalkyl sites, preferably carboxymethyl sites, carboxyethyl sites or carboxypropyl sites. The chemical modification may be effected by reaction with sodium monochloroacetate in sodium hydroxide, thereby to provide carboxymethyl sites.

In another variant thereof the cationic adsorbing sites are sulfate sites. The chemical sulfate sites comprise sulfate esters derived from hydroxyl groups of the cellulose in the substrate and from sulfate reagents. The chemical modification may be effected by reaction with sulfuric acid, or chlorosulfuric acid in an organic solvent, sulfur trioxide complexes with a tertiary amine, dimethylsulfoxide or amide in water or in an organic solvent, the reaction product of sodium nitrate and sodium bisulfate, or urea and sulfamic acid; preferably, the chemical reaction is effected by reaction with a sulfamic acid-urea aqueous solution.

In yet another embodiment of the method of this invention, the supporting step includes the prelimary step, before the supporting step, of cutting the wetted substrate to a selected length. Such step of supporting the substrate in the material which substantially inhibits the escape of such solution or solutions from the environment of the substrate, may be provided by supporting short lengths of the wetted cloth on rigid glass or synthetic plastic plates; or by supporting short lengths of wetted cloth within a flaccid synthetic polymer sealed envelope; or by supporting short or long lengths of the wetted cloth within a polyethylene sheet in the form of a long tube with its ends sealed, and which is folded, accordion style along the sealed ends; or by supporting long lengths of the wetted cloth within a long tube of polyethylene with its ends sealed and which is rolled on a hollow mandrel.

In one preferred embodiment of the method of this invention, where a cutting step is performed prior to supporting step, the cutting step may be provided by cutting the cloth into short lengths up to about 1 meter, or into long lengths of about 5 to about 10 meters or more, or into longer lengths of greater than about 10 meters.

In still another embodiment of the method of this invention, the curing step may be provided by supporting the cloth on rigid glass or synthetic plastic plates while resting on spaced-apart shelves, or in a pile one atop another, in an oven with air circulation at a temperature of up to about 100° C. or may be provided by supporting short lengths of wetted cloth within individual sealed synthetic polymer tubes, while resting on spaced-apart shelves in an oven with air circulation at a temperature of between about 30° C. to about 50° C.; or may be provided by supporting long lengths of wetted cloth within long tubes of synthetic polymer with the ends sealed and folded, accordion-style at the seals, while being in a pile in an oven with air circulation at a temperature of between about 30° C. to about 50° C.; or may be provided by supporting long lengths of the wetted cloth in an oven with air circulation at a temperature of between about 30° C. to about 50° C. while the cloth is rolled on a rotatable mandrel having spaced-apart rotatable end shafts, e.g. where the rotatable mandrel is polytetrafluoroethylene (e.g., TEFLON TM) coated.

In yet another embodiment of the method of this invention, the washing step may be conducted in a centrifugal washer, the manner of operation of the centrifugal washer being either (i) so as to spray a washing solution on the cured cloth from a rotating hollow shaft, or (ii) so as to spray a washing solution on the cured cloth from a rotatable hollow shaft while the cured cloth is also subjected to centrifugal rotation. Preferably, the washing is effected with water or aqueous ethanol or aqueous HCl of concentration about 0.5N or aqueous NaOH of concentration about 0.5N.

In a still further embodiment of the method of the invention the method includes continuously-passing the cloth through a bath of a first selected chemical reactant solution and continuously-squeezing excess solution from the cloth while assuring that the solution is uniformly-adsorbed within the cloth, the uniform adsorption preferably being achieved by alternatively applying pressure to the cloth and releasing the pressure from the same region of the cloth.

In a still further embodiment of the method of this invention, the method may include the step of continuously-passing the cloth through a bath of a first selected chemical reactant solution, continuously-squeezing excess solution from the cloth while assuring that the solution is uniformly-adsorbed within the cloth, continuously passing the so-adsorbed cloth in contact with an applicator to apply a second selected chemical reactant solution, and continuously-squeezing excess solution from the cloth while assuring that the two solutions are uniformly-adsorbed within the cloth, the second selected chemical reactant solution being uniformly-adsorbed within the cloth within which the first selected chemical reactant solution is uniformly-adsorbed, by alternately applying pressure to the cloth and releasing the pressure from the same region of the cloth.

In a further embodiment of the method of this invention, the method may further include the step of passing the saturated cloth between the nip of two counter-rotatable rollers before the cutting step.

In a still further embodiment of the system of this invention, the suitable backing which substantially inhibits the escape of such solution from the environment of the substrate may be a glass or synthetic plastic sheet slightly larger in area than the area of a substrate supported thereby by being slightly longer and slightly wider than the substrate; or it may be a polyethylene sheet slightly larger in area than the area of a substrate supported thereby by being slightly longer and slightly wider than the substrate; or it may be a synthetic plastic film envelope within which individual discrete lengths of the substrate are placed, which are then individually sealed; or it may be a polyethylene flat tube envelope within which a plurality of discrete lengths of the substrate are placed, which are then separated by seals and which are finally folded into an accordion or serpentine configuration at the seals; or it may be a cylindrical base having a slot within which one end of a combination of one discrete length of a synthetic plastic sheet with a discrete length of the substrate therebetween is inserted, following which the combination is wound therein, following which the wound combination is mounted between two roller ends to provide a mandrel having a shaft at each end for rotatably-mounting in the dryer means; or it may be a cylindrical base formed of polytetrafluoroethylene and having a slot within which one end of a combination of one discrete length of the polyethylene film with a discrete length of the substrate therebetween is inserted, following which the combination is wound therein, following which the wound combination is mounted between two roller ends to provide a mandrel having a shaft at each end for rotatably-mounting in the dryer means.

In one preferred embodiment of the system of this invention, the knife means may comprise a guillotine knife.

The system of this invention may further be provided with guiding means which comprises freely-rotatable rollers. Preferably those roller means may include controls for alternately applying pressure and releasing pressure on the substrate, thereby intimately-dispersing the chemical reactants therein.

The system of this invention may be further be one in which the second container may comprise a cylinder terminating in a frusto-conical end provided with an outlet slot, and combined with a spaced-apart roller means below the outlet slot.

The curing means in the system of this invention may comprise an oven having means to stack a plurality of supported sheets of the wetted substrate; or it may comprise an oven having spaced-apart shelves therein for stacking a plurality of supported sheets of the wetted substrate; or it may comprise an oven having the interior of which is adapted to be filled with individual synthetic plastic tubes within which individual lengths of wetted substrate has been sealed; or it may comprise an oven, the interior of which is adapted to be stacked with a plurality of the wetted substrates sealed in lengths of synthetic plastic film which have been folded into a serpentine or accordion configuration at the seals; or it may comprise an oven provided with a plurality of rotatable bushings adapted to rotate an associated plurality of mandrels having a shaft at each end thereof. Such oven should be one in which heated air is adapted to be passed through with efficient air circulation therein.

The washer means in the system of this invention may comprise a centrifugal washer having washer inlet spraying means and a centrifugally-rotatable basket.

In the system of this invention, the centrifugal washer may include a cylindrical casing having central liquid inlet means and tangential liquid outlet means, a hollow perforated tube connected to the central liquid inlet means and having mechanism for rotating the hollow perforated tube, a perforated basket adjacent the cylindrical casing and having mechanism for rotating the perforated basket, and having means for hanging or otherwise placing the cloths to be washed evenly within the perforated basket.

The means for drying in the system of this invention may comprise an open air dryer.

GENERALIZED DESCRIPTION OF THE INVENTION

By embodiments of the present invention, dialkylaminoalkyl, preferably diethylaminoethyl (DEAE), and carboxyalkyl, preferably carboxymethyl (CM), or sulfate ($SO_3$-) forms of dressings have been provided so that anionic drugs can be adsorbed onto DEAE-dressing and cationic drugs can be adsorbed onto CM-dressing or $SO_3$- dressings and be held thereon by ionic bonds. Most of proteases are positively charged and thus can be adsorbed to CM-dressing or $SO_3$-dressings.

Ionic forms of dressing have been provided by this invention to which a variety of ionic drugs (antibiotics, healants, anesthetics, etc.) as well as enzymes can be adsorbed. When applied on weeping wounds or burns, the drug will be released in controlled amounts by ion exchange with ions in the body exudate in proportion to the amount of exudate. Such a controlled release will reduce unnecessary exposure to drugs and thus to allergic reactions. Fibrinolytic enzymes can be adsorbed to the ionic dressing and may be used to dissolve fibrous or purulent accumulation and reduce inflammation. Ionic irritants generated will be adsorbed to the dressings. Use of these dressings will permit rapid and gentle application and removal of drugs and thus facilitate treatments in emergency situations, e.g. accidents, earthquakes, fires and wars.

The wound dressings of this invention can also be used to treat skin diseases, e.g., acne, or inflamation. They may also find the same applications as cosmetics, as was disclosed for the microspheres patented by Advanced Polymer Systems, as U.S. Pat. No. 4,690,825, as was described in the Mar. 9, 1988 issue of Chemical Week.

In the method embodiments of this invention, the cloth may be supported by being placed in a plastic bag or on a plate made of TEFLON (registered Trade Mark for polytetrafluoroethylene) or of rubber and caused to be folded in a back-and-forth, or serpentine, or accordian, movement.

For a substrate of about 1 meter in width, a short length may be about 1 meter, while a long length may be about 5 meters or about 10 meters or even more, depending on the nature of the subsequent incubation, curing and drying steps. It is important that the reactant should not completely evaporate during curing reaction time, which may be from about 1.5 to about 2 hours.

During this supporting stage, the reactant solution does not completely evaporate, and the reactant chemical does not completely disappear during the curing stage of about 1.5 to about 2 hours. The supported cloth may be cured while being supported on rigid glass or synthetic plastic plates while resting on spaced-apart shelves in an oven with efficient air circulation at a suitabletemperature. For DEAE-cloths and CM-cloths, the suitable temperature would range from about 20° C. to about 50° C., preferably about 30° C., for times of up to about 3 hours. For $SO_3$-cloth, the suitable temperature can be as high as about 100° C. For DEAE-cloth and CM-cloth, the chemically-treated cloth may be cured, but not completely dried, while being stacked in an oven having efficient, circulating air ventilation at a temperature of about 30° C. to about 50° C. For $SO_3$-cloth, the chemically-treated cloth should be substantially completely dried while it is stacked in an oven with efficient circulating air ventilation, at a temperature up to about 100° C.

BRIEF DESCRIPTION OF THE DRAWINGS

Reference will now be made to the accompanying drawings wherein like reference numerals throughout the various figures denote like elements, and wherein.

DESCRIPTION OF PREFERRED EMBODIMENTS OF CLOTHS

Figure 1:
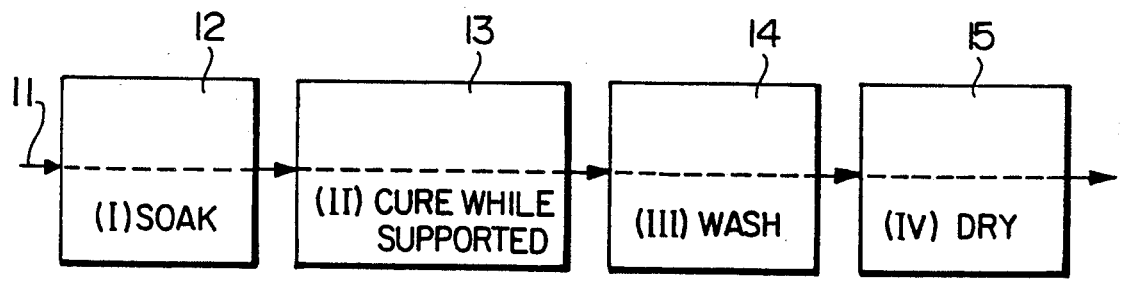
FIG. 1 is a schematic block diagram representing a commercially-viable method of one embodiment of this invention for preparing a derivatized substrate according to another embodiment of this invention used to prepare the wound dressing of another embodiment of this invention.

Before describing the apparatus embodiments of this invention, the following description of the chemical processes for the preparation of the derivatized substrates will be given.

(i) Generalized Description for the Preparation of DEAE-Cloths, CM-Cloths, and $SO_3$-Cloths For DEAE, the nonwoven rayon/polyester cloths (SONTARA 8407 or SONTARA 8423) are placed on a flat polyethylene sheet and wetted with diethylaminoethyl chloride solution (e.g., 20%) in $H_2O$ and then soaked with NaOH solution (e.g., 15%) saturated with $Na_2SO_4$. For CM, the cloths placed on a polyethylene sheet are soaked with a sodium mono-chloroacetate solution (e.g. 20%) in a NaOH solution (e.g. 15%).

Another polyethylene sheet is placed on top of the so-treated cloths The sandwiched cloths are incubated at 30° C. for suitable lengths of time (normally less than 2 h). The DEAE cloths are washed with $H_2O$, 0.5N NaOH and $H_2O$. The CM cloths are washed with $H_2O$, 0.5N HCl and $H_2O$. Both types of cloths are air-dried. The degree of modification is controlled by time and the modified cloths must have good adsorption capacity (measured by adsorption of bovine serum albumin) and pliability and softness for contact with skin. Adsorption of fusidic acid to DEAE cloth and chlorohexidine to CM cloths has been used as model systems. The modification reaction can be carried out at any temperature between 20° C. and 50° C.

A dialkylaminoalkyl cloth other than DEAE-cloth, or a carboxyalkyl cloth other than CM-cloth, may be prepared in the same way as generally described above by the use of the corresponding dialkylaminoalkyl halide or by the use of a corresponding salt of a monohalocarboxylic acid.

For $SO_3$-cloths, the sulfate group may be prepared by forming a sulfate ester between hydroxyl groups of the cellulose in the substrate and sulfate reagents. Examples of suitable sulfate reagents include sulfuric acid, chlorosulfuric acid in an organic solvent, sulfur-dioxide complexes with tertiary amines, e.g. triethylamine, dimethylsulfoxide in water or in an organic solvent, dimethylamide in water or in an organic solvent, or the reaction product of sodium nitrate and sodium bisualfate. Preferably the reagent is a sulfamic acid-urea aqueous solution.

The physiologically- or biologically-active agent can be adsorbed in the dialkylaminoalkyl-cloth, in the carboxyalkyl-cloth or in the $SO_3$-cloth by soaking the respective cloth in an aqueous or aqueous alcoholic solution of the active agent.

Specific Description for the Preparation of DEAE-Cloth CM-Cloth, and $SO_3$-Cloth The following are Preparation Example I, namely a laboratory scale procedure, for the preparation of DEAE-cloth, CM-cloth and $SO_3$-cloth and Examples 2-4, which are embodiments of wound dressings of this invention.

PREPARATION EXAMPLE I

Preparation of DEAE-Cloth, CM-Cloth, and $SO_3$-Cloth

Nonwoven rayon/polyester blend (70/30) fabric (SONTARA 8407) was used to prepare DEAE-cloth, CM-cloth and $SO_3$-cloth. This fabric has a unit weight of 5.1 mg per $cm^2$, and its apertured style permits good aeration when applied to skin.

For DEAE-cloth, the above-described cloth was placed on an alkali-resistant thin plastic sheet (e.g. polyethylene), uniformly moistened with 20% (w/v) diethylaminoethyl chloride hydrochloroide in $H_2O$ (0.04 ml per $cm^2$ of cloth), and then with 15% (w/v) NaOH in a saturated $Na_2SO_4$ aqueous solution (0.01 ml per $cm^2$ of cloth). A second plastic sheet was placed on the top of the cloth. This sandwiched cloth was multiplely layered between two heavy plates (glass, plastic or metal), and incubated at 30° C. for various lengths of time (e.g. 0.5 h. to 2.5 h.). The cloth was then washed with water, then with 0.5N NaOH, and water (until it had a neutral pH) and then was air-dried.

For CM-cloth, the above-described cloth, placed on a plastic sheet, was uniformly moistened with 20% (w/v) sodium monochloroacetate in 15% (w/v) NaOH (0.05 ml per $cm^2$ cloth) and was then covered with a second plastic sheet. Multiple layers of the sandwiched cloth were incubated as described above for the preparation of the DEAE-cloth at 30° C. for various lengths of time (e.g. 0.5 h. to 3 h.). The cloth was then washed with water, then with 0.5N HCL and water (until it had a neutral pH), and then was air-dried.

For $SO_3$-cloth the above described cloth placed in the plastic sheet, was uniformly moistened with a sulfamic acid-urea aqueous solution of 20% (w/v) sulfamic acid and 80% (w/v) area in water, and was then covered with a second plastic sheet. Multiple layers of the sandwiched cloth were incubated as described above for the preparation of the DEAE-cloth, but at 100° C. to be substantially completely dried for various lengths of time (e.g. 0.5 h. to 3 h.). The cloth was then washed with water, then with 0.5N HCL and finally with water (until it had a neutral pH), and then was air-dried.

The degree of cloth modification was measured by adsorption of bovine serum albumin to DEAE-cloth and egg white proteins to CM-cloth or $SO_3$-cloth. Longer reaction times (at 30° C.) produced a cloth of higher protein adsorption, reaching a maximum adsorption of 5 mg protein per $cm^2$ of cloth (1 g protein per/g. cloth). However, overmodification generated undesirable texture (e.g. it was too hard for contact with skin or was too soft for handling). The reaction times of 1.5 h.

for DEAE-cloth and 2 h. for CM-cloth or SO3-cloth were used to obtain suitable pliability and softness (with protein adsorption capacity of 2 mg/cm$^2$).

(A) - Preparation of DEAE-Cloth - Procedure (A)

A 2×2 cm square piece of SONTARA 8407 was placed on a polyethylene sheet which was placed over a glass plate. 150 µl of 20% DEAE (e.g. 20% diethylaminoethylchloride hydrochloride) solution was applied evenly to provide a quite wet condition to the cloth. 50 µl of 15% alkaline solution (e.g. 15% NaOH saturated with Na$_2$SO$_4$) was further spread evenly on the cloth. The wet cloth was then sandwiched between polyethylene sheets and glass plates and was wrapped in a plastic bag. It was then heated in an oven at 30° C. for 1.5-2.0 hours.

It was then washed with water first by draining, then with 0.5N. HCl and finally over a glass filter. It was then air-dried. The texture of the product was soft.

(B) - Preparation of DEAE-Cloth - Procedure (B)

A 2×2 cm square piece of SONTARA 8407, 100 µl of 20% DEAE solution was applied carefully in an even manner by an automatic pipette and the cloth was folded once, pressed between polyethylene sheets with the fingers to assist the solution in being distributed evenly by capillary effect enforced by pressure. Then about 100 µl of sodium sulfate (Na$_2$SO$_4$) saturated in 15% sodium hydroxide (NaOH) solution was applied evenly and was then allowed to stand for enough time (about 15 sec) to distribute itself by capillary effect with the assist of applying light pressure with the fingers (press and release several times). The cloth was then unfolded.

The cloth was then sandwiched between polyethylene sheets and outer glass plates, and was wrapped in a plastic bag (e.g., BIO HAZARD TM autoclave bag).

The cloth was then heated at about 30° C. for about 1.5 hour in an oven. (Longer times will bring more modification with texture deterioration) The cloth was then washed in water by decantation and then on a filter and was finally air-dried.

By above method of preparation, the 2×2 cm square piece of cloth absorbed 21.3 mg of egg white protein.

The uniformity of modification of the cloth was determined by a dye absorption test. For example, the following table holds true for dyes, and colour produced:

| AFTER TREATMENT | | CONTROL (NO TREATMENT) |
|---|---|---|
| Dye | Colour | Colour |
| Phenol red | dark red | colourless |
| Rhodamine B | colourless | colourless |
| Nile blue | colourless | navy blue |
| Coomasie blue G | blue | light blue |
| Acid Fuchsin | pink | faintly pink |

(C) - Preparation of CM-Cloth

A 2×2 cm square piece of SONTARA 8407 was placed on a polyethylene sheet which was on top of a glass plate. 200 µl of monochloroacetate (e.g. 20% sodium monochloroacetate in 15% NaOH) solution was applied evenly.

This saturated cloth was covered by a polyethylene sheet and a glass plate (using the sandwich method), was wrapped in a plastic, e.g., a polyethylene bag, and was heated at about 30° C. for about 2 hours in an oven. It was then washed sequentially with water, or with 0.5N NaOH and with water and finally was air-dried.

The uniformity of modification of the cloth was determined by a dye absorption test, with the following results:

| AFTER TREATMENT | | CONTROL (NO TREATMENT) |
|---|---|---|
| Dye | Colour | Colour |
| Phenol red | colourless | colourless |
| Rhodamine B | pink | colourless |
| Nile blue | dark navy blue | navy blue |
| Coomasie blue G | colourless | light blue |
| Acid Fuchsin | colourless | faintly pink |

A 2×2 cm square piece of SONTARA 8407 or of SONTARA 8423 was placed flat at the bottom of a scintillation vial (about 2.5 diameter, about 5.5 cm high). 150 ul of sulfamic acid-urea solution was applied evenly. The sulfamic acid-urea solution had a pH of 1-2 and was composed of 0.2 g of sulfamic acid and 0.8 g of urea dissolved in 5 ml water. For derivatization, adjustment of pH is not crucial, but for the stability of the derivatized cloth to be formed, it is advisable to raise the pH to close to neutral, e.g., the addition of a sufficient amount of about 10% NaOH to change the pH of the solution above-described to pH 6. The above-described wet cloth was heated to about 100° C., using a block heater, in the scintillation vial without the cap on for about 4.5 hours. The cloth was substantially completely dried during this heating reaction. (Excess reaction resulted in deterioration of cloth texture). The so-derivatized cloth was washed well with water (if necessary it may be washed with 0.5N. NaOH and water). The washed product was then air-dried.

The dye tests gave the same results as described above for CM-cloth. For example, Rhodamine B gave a pink colour but Phenol red was colourless.

Preparation of Ionic Dressings of Embodiments of the Invention

EXAMPLE 1

Adsorption of fusidic acid and chlorhexidine

Currently, gauze dressings which have been impregnated with an ointment of fusidic acid or chlorhexidine are used to treat wounds topically. Adsorption of these antibiotics to the ionic dressings according to aspects of this invention was determined. Segments (1 cm square) of DEAE-, CM- and unmodified cloth were soaked in 1.0 ml/cloth segment of 10 mg/ml sodium fusidate or 10 mg/ml chlorhexidine digluconate for 2 h. at room temperature. The segments were then washed with water.

Each segment was then soaked in 1.0 ml of porcine serum or Krebs phosphate Ringer to simulate a heavy bleeding situation (at the wound site).

The particular Krebs phosphate Ringer solution used herein had the following composition:

| | | | |
|---|---|---|---|
| | 100 Vol. | 0.154 M | NaCl |
| | 4 Vol. | 0.154 M | KCl |
| | 3 Vol. | 0.110 M | CaCl$_2$ |
| | 1 Vol. | 0.154 M | KH$_2$PO$_4$ |
| | 0.5 Vol. | 0.154 M | MgSO$_4$ |
| and | 0.45 Vol. | 0.154 M | MgCl$_2$ |

The amount of the respective antibiotics released were estimated by standard inhibition zone assay using an *Escherichia coli* ESS strain as an indicator, and are shown in Table 1.

TABLE 1

Antibiotics (mg) Released From Ionic Dressings (1 cm²)

| Elution time (h.) | Fusidate from DEAE | | Chlorhexidine from CM | |
|---|---|---|---|---|
| | Serum | Ringer Solution | Serum | Ringer Solution |
| 0.5 | 0.25 | 0.5 | 0.1 | 0.25 |
| 1.5 | 0.5 | 0.5 | 0.25 | 0.3 |
| 24 | 0.63 | 0.75 | 1.0 | — |

Table 1 shows that the serum gradually released both antibiotics from the ionic dressings. The Ringer solution more rapidly released similar amounts of antibiotics. Since the release is due to ion exchange, macromolecular ions in the serum do not seem to be as efficient as inorganic ions in the Ringer solution. The underivatized cloth (as a control but similarly treated with the antibiotics) released negligibly small amounts of fusidate and less than a tenth the amounts of chlorhexidine released by the CM dressing.

The air-dried antibiotic dressings were stored in a light-free container at room temperature. After 4 months, the activities of the antibiotics released by the serum were determined. Both the fusidate and the chlorhexidine dressings exhibited nearly the original activity of antibiotics as described above.

EXAMPLE 2

Adsorption of Other Drugs by Ionic Bonding

Segments (1 cm square) of DEAE-, CM-cloth and SO$_3$-cloth were soaked in 1.0 ml of 10 mg/ml of a variety of topical drugs for 2 h. at room temperature, washed with water, and then soaked in 1 ml of Krebs Ringer phosphate solution for 2 h. at room temperature. The amount of drugs released after 2 h. were estimated by ultraviolet absorption (at wavelengths between 200 to 260 nm) after diluting the extract to linear concentration vs. absorption ranges.

Table 2 (below) illustrates that all the anionic drugs tested adsorbed to the cationic DEAE-cloth, that all the cationic drugs tested adsorbed to the anionic CM-cloth, and that the adsorbed drugs can be extracted by Krebs Ringer phosphate solution. However, the results shown in Table 2 represent the amounts released with a limited volume of the Ringer solution for 2 h. and do not represent maximum adsorption of drugs.

Table 3 (below) illustrates that, under the same test conditions, all the cationic drugs tested adsorbed to the anionic CM-cloth and the anionic SO$_3$-cloth, and that the adsorbed drugs can be extracted by Krebs Ringer solution.

TABLE 2

Drug Released Into 1 ml Krebs Ringer Solution

| Cloth | Drug | Solvent for drug adsorption | Drug released Ringer (mg) |
|---|---|---|---|
| DEAE | | | |
| | Sodium Fusidate | H$_2$O | 0.52 |
| | Pseudomonic acid | Methanol | 0.33 |
| | Sodium Ceftriaxone | H$_2$O | 0.5 |
| | Nafcilin | " | 0.36 |
| | Adenosine | " | 0.76 |
| | diphosphate | | |
| | Nystatin | Methanol | 0.2 |
| | Undecylenic acid | H$_2$O | 0.2 |
| | Salicylic acid | Methanol | 0.25 |
| | Salicylsulfuric acid | H$_2$O | 0.25 |
| | Nicotinic acid | " | 0.28 |
| CM | | | |
| | Chlorhexidine digluconate | H$_2$O | 0.31 |
| | Bacitracin | " | 0.72 |
| | Chlortetracycline | " | 0.48 |
| | Gentamycim sulfate | " | 0.44 |
| | Kanamycin sulfate | " | 0.71 |
| | Neomycin B sulfate | " | 0.24 |
| | Polymyxin B sulfate | " | 0.25 |
| | Streptomycin sulfate | " | 1.0 |
| | Tetracycline | Methanol | 0.012 |
| | Amphotericin B | " | 0.02 |
| | Clotrimazole | " | 0.02 |
| | Micronazole | " | 0.01 |
| | Cysteine | H$_2$O | 0.12 |
| | Glycine | " | 2.0 |
| | Threonine | " | 3.0 |
| | Lidocaine | " | 0.72 |

TABLE 3

| Drugs | Wavelength used A (nm) | Extracted from SO$_3$-cloth (2 × 2 cm) (mg) | Extracted from CM-cloth (2 × 2 cm) (mg) |
|---|---|---|---|
| chlorohexidine digluconate | 230 | 0.37 | 0.15 |
| Neomycin B sulfate | 200 | 0.88 | 0.8 |
| Epinephrine | 230 | 0.09 | 0.1 |
| Serotomin | 220 | 0.15 | 0.1 |

EXAMPLE 3

Adsorption of trypsin and plasmin

Trypsin is capable of removing proteinaceous material from a wound. It is positively charged at a neutral pH, and therefore should be adsorbed to anionic CM-cloth. A 1 cm square segment of CM-cloth was soaked in 1 ml (per segment) of 1 mg/ml trypsin in 0.02M sodium phosphate buffer (pH 7.0). The segment was washed with water, suspended in 1 ml of the Ringer solution for trypsin activity. One segment of the cloth having trypsin absorbed therein showed 150 BAEE units.

Plasmin (or fibrinolysin) occurs in blood and is responsible for fibronolysis, i.e. dissolution of blood clots by the proteolytic degradation of fibrin to soluble peptides. A 1 cm square segment of DEAE-cloth was soaked in 1 ml (per segment) of 0.4 mg (1.3 U.)/ml of plasmin (plasminogen activated by streptokinase) solution. The segment was washed with water and suspended in a standard clot for activity to lyse the clot.

One segment of the cloth to which plasmin was adsorbed, showed 1 U. activity.

Utility of Dressings of Preferred Embodiments

As noted above, immobilized (adsorbed) enzymes can be used as adjuncts to antibiotic prophylaxis of surgical wounds as well as infected wounds as they show an anti-inflammatory activity. CM-dressing or $SO_3$- dressing should also adsorb cationic irritants, e.g. amines which may be generated from enzyme hydrolysis or infection. These materials can be removed with the dressing. Furthermore, CM- dressing or $SO_3$- dressing will likely adsorb a large amount of fluid and also exhibit a blood coagulating activity.

Another expected advantage of these drug systems is that the adsorbed drugs will be more stable than free drugs either in solution or suspension. Unlike dressings impregnated with drug ointments, the ionic dressings, when applied in dry forms, adsorb fluid weeping from the damaged tissues and provide better air circulation (breathability) which is often desired for the wound treatment.

As described above, it has been found that the adsorbed drugs are elutable with porcine serum and with Ringer solution and the eluted drugs have been shown, by inhibition zone assay, to inhibit the growth of *Escherichia coli*. This suggests that upon application to weeping sites the dressings are capable of releasing drugs by ion exchange with ions in the blood.

(A) ADP-DEAE-Cloth

Red cells are the main source of ATP and ADP in haemostasis. 90% of the admin myceloid in blood is in the red blood cells and 10% thereof is in the platelets. ADP is not further degraded in the clotting process and plays a major important role in blood clotting at cuts. For example, thrombin can initiate aggregation of platelets, but without ADP this process will not occur. ADP is essential for fibrin formation from thrombin. Thrombin starts the aggregation of platelets which adhere to collagen fibres and releases ADP (i.e., haemostatic plug formation). After a cut, in 2 to 3 seconds, only small traces of ADP and mostly ATP are in o blood; by 20 seconds, half of the ATP is transformed to ADP; and by 70 seconds, most of the ATP is in ADP form. Thus, during 1 to 4 minutes after bleeding commences, a haemostatic plug will start to form. In standardized conditions, cuts 5 mm long×1 mm deep at 40 mm Hg will take 4 to 7 minutes to stop bleeding. Supplying excess ADP immediately after the cut occurs, through the use of an ADP dressing will help to accelerate fibrin formation and will stop bleeding faster.

ADP Adsorption to DEAE-Cloth 50 mg. ADP in 250 µl water was applied evenly on 2×2 cm DEAE-SONTARA 8423 cloth or on 2×2 cm DEAE-SONTARA 8407 cloth and was kept at room temperature for one hour. The high concentration of ADP enabled the ADP to be quickly absorbed to the DEAE-SONTARA cloth. The so-produced cloth was then washed well with water. It was found that 6.8 mg of ADP was absorbed on 2×2 cm cloth.

Effect of Concentration of ADP on DEAE-Cloth in Constant Incubation Time

Adsorption of different concentrations of ADP at 17° C. for 3 hours incubation on a 2×2 cm DEAE-cloth were studied, with the following results:

| | ADP Amount (mg) in 250 ml applied on 2 × 2 cm DEAE-cloth | ADP absorbed on 2 × 2 cm DEAE-cloth |
|---|---|---|
| 1 | 50 mg. | 4.16 mg. |
| 2 | 20 mg. | 4.24 mg. |
| 3 | 15 mg. | 3.52 mg. |
| 4 | 10 mg. | 2.88 mg. |
| 5 | 5 mg. | 1.92 mg. |

The measurements of ADP adsorbed on DEAE were conducted by UV absorption measurements at $A_{260nm}$, of ADP extracted by Krebs Ringer solution (4 ml/2×2 cm cloth) and calculated from the standard adsorption curve.

Effect of Incubation Time on ADP Absorption on DEAE-Cloth at Constant ADP Concentration A study of the adsorption of ADP on DEAE-cloth was investigated as follows:

5 mg ADP in about 250 ml was applied on 2×2 cm DEAE-SONTARA 8423 cloth or on 2×2 cm DEAE-SONTARA 8407 cloth and was incubated at about 25° C. for different lengths of time. The adsorbed ADP was extracted and measured in the same manner as described above in section (ii).

The results were as follows:

| | Incubation time (hr.) | ADP absorbed on 2 × 2 cm DEAE-cloth (mg.) |
|---|---|---|
| 1 | 2 hr. | 2.50 mg. |
| 2 | 3 hr. | 3.00 mg. |
| 3 | 4 hr. | 3.28 mg. |
| 4 | 5 hr. | 3.48 mg. |
| 5 | 6 hr. | 3.68 mg. |
| 6 | 24 hr. | 4.80 mg. |

It is noted that, because the incubation temperatures were different, the amount of ADP adsorbed was slightly different. However, as shown above, even a low ADP concentration close to DEAE-cloth maximum absorption capacity, can provide maximum absorption if longer incubation times, e.g., 24 hours are used.

Gradual Release of ADP from ADP-DEAE-CLOTH

Simulated conditions for the gradual release of ADP was studied in the following manner:

1×1 cm of ADP-DEAE-SONTARA 8423 cloth or 1×1 cm of ADP-DEAE-SONTARA 8407 cloth was evenly-applied with 50 ml of basic Krebs Ringer solution or porcine antiserum and was incubated at room temperature for five minutes. Then the solution on the cloth was transferred onto a pair of 2.3 cm diameter 3 MM Qualitative filter papers which were cut into half size and folded as a sandwich. The half-cut filter papers were then transferred into a test-tube and ADP was extracted by 2 ml of basic Krebs Ringer solution. This procedure was then repeated ten times. The UV absorption of the extracted ADP was measured at $A_{260nm}$ by diluting it two times.

Figure 10:
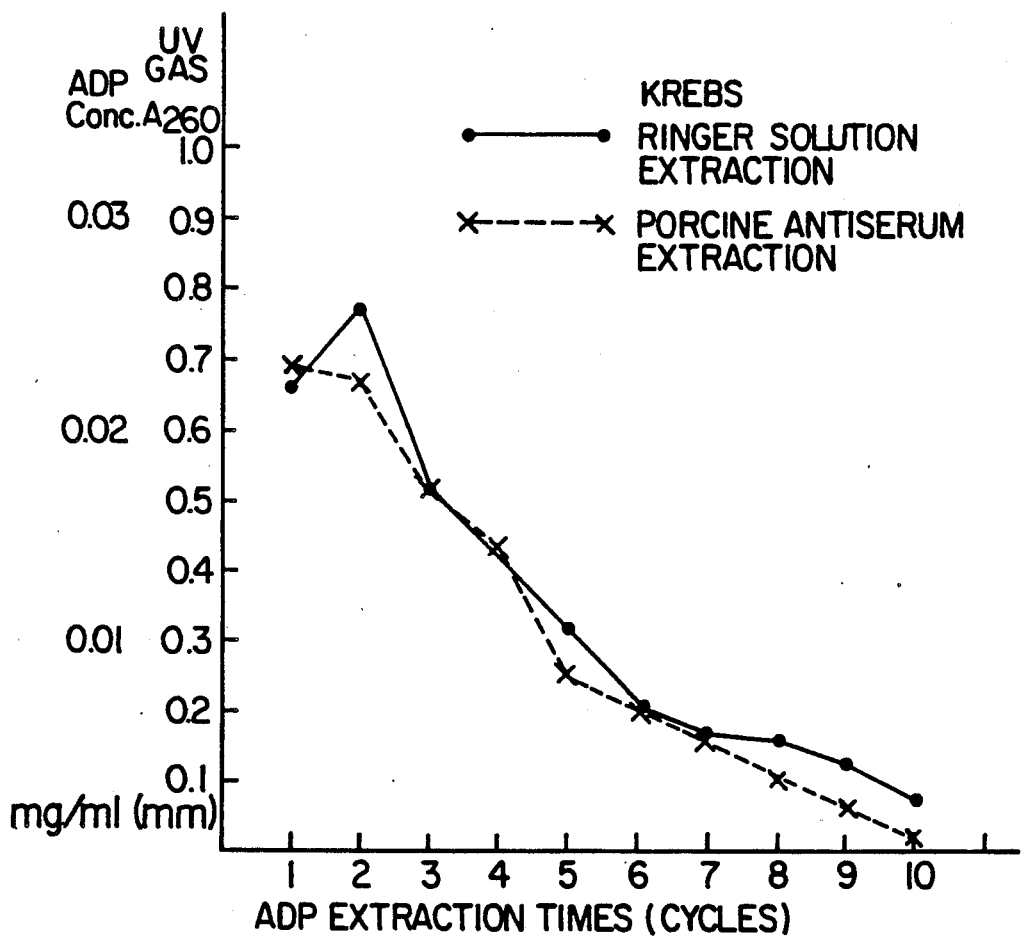
FIG. 10 is a graph of ADP concentration as ordinate and ADP extraction times as abscissa, for ADP-DEAE-cloth.

The results were plotted as shown in the graph in FIG. 10. From the graph, it is seen that ADP on DEAE-cloth may be extracted, and that Krebs Ringer solution (shown as the solid line) and porcine serum (shown as the broken line) gave almost identical results.

Thus, Krebs Ringer solution and porcine antiserum extraction of ADP demonstrate a similar condition, i.e., that salts in the blood are ion-exchanging with ADP on the DEAE-cloth.

Bleeding Time Test

The effect of ADP-DEAE-cloth in an actual bleeding condition was tested. A method using the SURGICUTT (Trade Mark of International Technidyne Corporation) specification was followed. SURGICUTT gives a uniform surgical incision 5 mm long×1 mm deep. It was used to make a horizontal incision parallel to, and approximately 5 cm below, the anticubital crease on the volar surface of the forearm by placing a sphygmomanometer cuff on the upper arm at 40 mm Hg. Every 30 seconds, blood from the incision was wiped away either by means of a gauze pad or by absorbent paper. The time was measured when the cut was closed and no more bleeding was observed. A statistical analysis revealed that the mean bleeding time for SURGICUTT of 4.5 minutes (SD 1.7 minutes) and a normal range of 1.1 to 7.9 minutes (reference - C. Smith, J. Med. Tech. 3 229–231 (1986)).

Following the specified method, it took 4.5 minutes a patient to stop bleeding time; application of 1×1 cm ADP-DEAE-SONTARA 8423 (1 mg ADP) on the fresh incision on the same patient enabled the bleeding to stop in 1.5 minutes.

Under the influence of 650 mg acetylsalicylic acid, (which has the function of reducing blood clotting), which was taken two hours before the test, the bleeding time was 5.7 minutes; with ADP-cloth application, bleeding time was reduced to 3.0 minutes. However, ADP-cloth which was stored at room temperature for more than one month took 4.5 minutes bleeding time. This result shows that the product should be kept in a freezer (or refrigerated) in a dry state.

ADP-DEAE-SONTARA 8407 Cloth (non-woven cloth in the form of net; all other ADP cloths were on SONTARA 8423) gave a 2.5 second bleeding time. This quick stoppage of bleeding could have been contributed by better airing and drying of the wound. However, SONTARA 8423 cloth itself can absorb large amounts of blood. Thus, a large profusion of blood will be better treated with ADP- DEAE-SONTARA 8423 cloth, and ADP-DEAE-SONTARA 8407 cloth may be more suitable for small amounts of bleeding or final stage of bleeding.

DESCRIPTION OF PREFERRED EMBODIMENTS OF SYSTEMS AND METHODS

Description of FIG. 1

FIG. 1 provides an overview of the method for preparing the derivatized substrate of the present invention. The first stage of operation on the base substrate 11, which may be a non-woven rayon or rayon/polyester cloth known by the trademark SONTARA is to pass to the SOAK zone (I), (12) e.g., in a continuous procedure by unwinding the substrate from a roll (not shown) and passing it into SOAK zone (I) (12). This SOAK zone (I) (12) may be one of the following two general types: it may be the soaking with one chemical solution as will be described further in Step (A) SOAKING in FIG. 2; or it may be the saturating first with one chemical solution in Step (A) SOAKING, the sequential applying of a second chemical solution in Step (B) APPLYING, and the intimate mixing of the two solutions within the substrate in Step (C) MIXING, all of which will be described further in FIG. 6.

The wetted substrate now passes to the CURE WHILE SUPPORTED zone (II) (13). This "curing while supported" may be done by continuously passing the wetted substrate while it is supported on a serpentine-configured suitable conveyor belt through an oven. However, it is preferred to cut the wetted substrate and to carry out one of the following sequence of steps: Step (B) CUTTING, Step (C) SUPPORTING and Step (D) REACTING as will be more fully described in FIG. 2; Step (B) CUTTING, Step (C) WRAPPING, Step (D) SEALING, Step (E) SUPPORTING and Step (F) REACTING, as will be more fully described in FIG. 3; Step (B) CUTTING, Step (C) WRAPPING, Step (D) SEALING, and Step (E) REACTING as will be more fully described with reference to FIG. 4; or Step (B) CUTTING, Step (C) BACKING, Step (D) PRELIMINARY ROLLING, Step (E) ROLLING, Step (F) MANDREL and Step (G) REACTING, as will be more fully described in FIG. 5.

The cured substrate now passes to the WASH zone (III) (14). If the CURE WHILE SUPPORTED procedure was carried out continuously, the washing may be carried out continuously by supporting the cured substrate on a foraminous conveyor and spraying wash water thereon from above and below. However, as described hereinabove, it is preferred that the cured substrate be of a discrete length. Accordingly, the preferred washing is achieved in Step (E) WASHING as will be more fully described in detail in FIG. 2.

After the cured substrate is washed it is dried in the DRY Zone (IV) (15). If the substrate is one which has been treated continuously, the drying may be carried out continuously, coupled with the step of rolling up the dried derivatized substrate on a roll (not shown). However, as described above, it is preferred that the cured washed substrate be of a discrete length. Consequently, the drying is preferably carried out by air drying as will be more fully described in FIG. 2.

Figure 2:
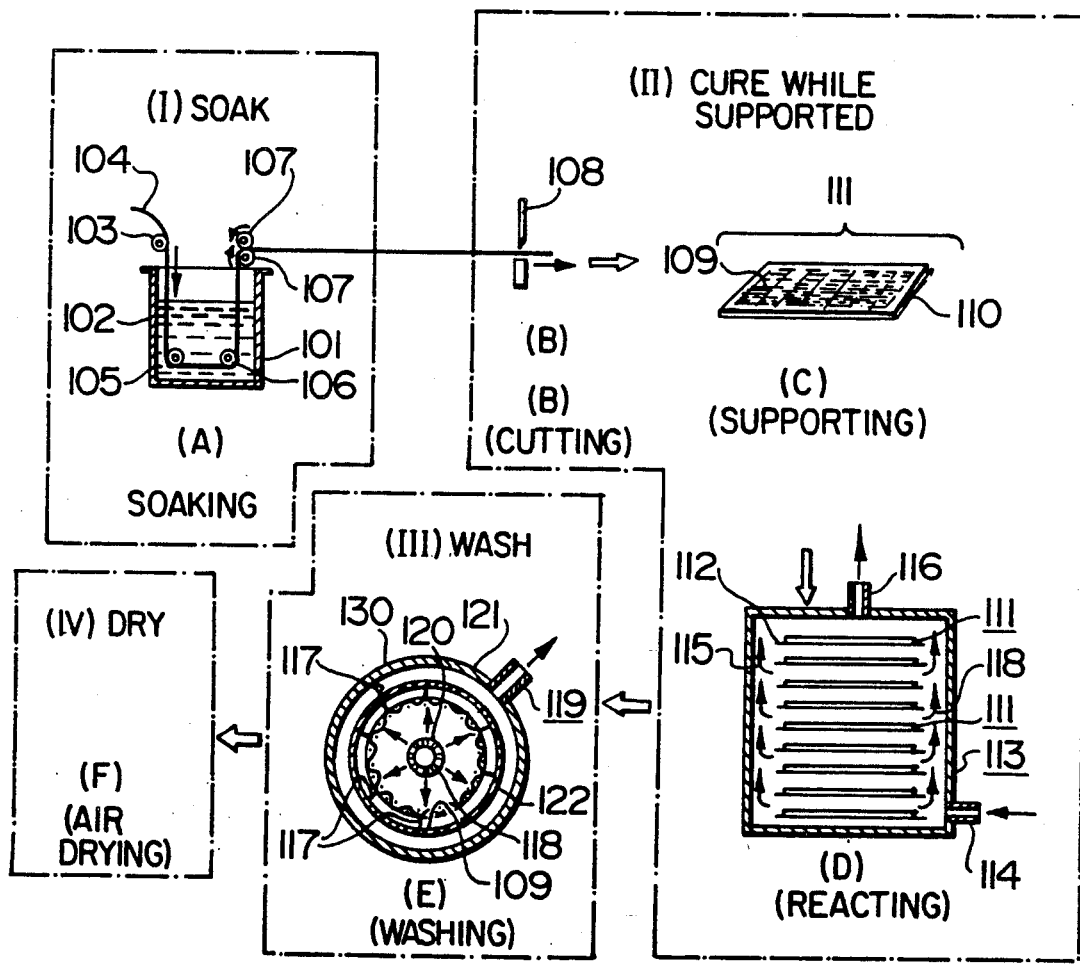
FIG. 2 is a schematic flow drawing showing one commercially viable method using one commercially useful system for producing one embodiment of a derivatized fabric, e.g., using a single reactant solution to provide a short length $SO_3$-cloth.

Description of FIG. 2

The first specific step depicted within block titled "(I) SOAK" comprises process STAGE A (soaking). As seen in FIG. 2, container 101 is provided for a suitable solution 102, e.g., sulfamic acid-urea solution to produce long length or short length $SO_3$-cloth. Above the container 101 is an entry-guiding roller 103 for a continuously-running length of cloth 104, e.g., the SONTARA 8423 or the SONTARA 8407, as described above. The cloth 104 is caused to enter the nether regions 105 of the container 102 and is held there in reacting contact with the solution by means of lower rollers 106. The cloth 104 then passes upwardly between the counter-rotating squeezing rollers 107 which are preferably adjustable to control the amount of the solution 102 which is retained in the cloth 104, and to assure that such reactant solution is uniformly absorbed in the cloth 104.

The second specific step depicted within block titled "(II) CURE WHILE SUPPORTED" is carried out as follows: cloth 104, with the solution 102 uniformly-absorbed therein is passed to process STAGE B (cutting) where a guillotine cutter blade 108 cuts the cloth into relatively short lengths 109.

At process STAGE C (supporting), the short lengths of cloth 104 having solution 102 uniformly-absorbed therein, and now designated as 109, are each placed atop a suitable plate 110, made of glass or of a synthetic plastic material, e.g., polyethylene, to form a unit 111.

At process STAGE D (reacting), a plurality of such units 111 is stacked on vertically-spaced-apart shelves 112 within a vertical air dryer 113. In air dryer 113, which may be an oven which produces a hot air flow from ambient air entering via inlet 114, or which may be a drying tower fed with hot air entering via inlet 114, and in which there is efficient air circulation, the derivatization of the cloth 109 is completed by the action of the hot air. For cloths which have been soaked with sulfamic acid-urea solutions to provide SO₃-cloth, the cloth must be substantially completely dried at this stage. The hot air follows an upwardly-flowing path, as seen by arrows 115 and the hot air, along with evaporated moisture, is vented by means of outlet 116. The hot air within the dryer 113 is preferably 100° C. to provide the SO₃-cloth.

The third specific step depicted within block titled "(III) WASH" is carried out as follows:

The derivatized cloth 109 is removed from the support of the plates 110 and is passed to process STAGE E (washing), where the cloth 109 is hung vertically on supports 117 and is disposed and evenly concentrically around a central hollow shaft 118 within centrifugal washer 119. One structure of such washer 119 will be described hereinafter with respect to FIG. 9. A water and/or basic washing solution, is fed in through a plurality of apertures 120 arrayed both circumferentially around shaft 118 and longitudinally along shaft 118. Shaft 118 is adapted to be rotatably-mounted within washer 119, so that it rotates and sprays a uniform amount of washing solution against the cloth 109. The cloth itself is hung on supports 117 within a concentric basket 122 which rotates along with shaft 118. The washing solution is withdrawn via drain 121.

The fourth specific step depicted within block titled "(IV) DRY" is carried out as follows:

After cloth 109 is washed in washer 119, it is removed and dried, preferably air-dried at process STAGE F (air drying).

Figure 3:
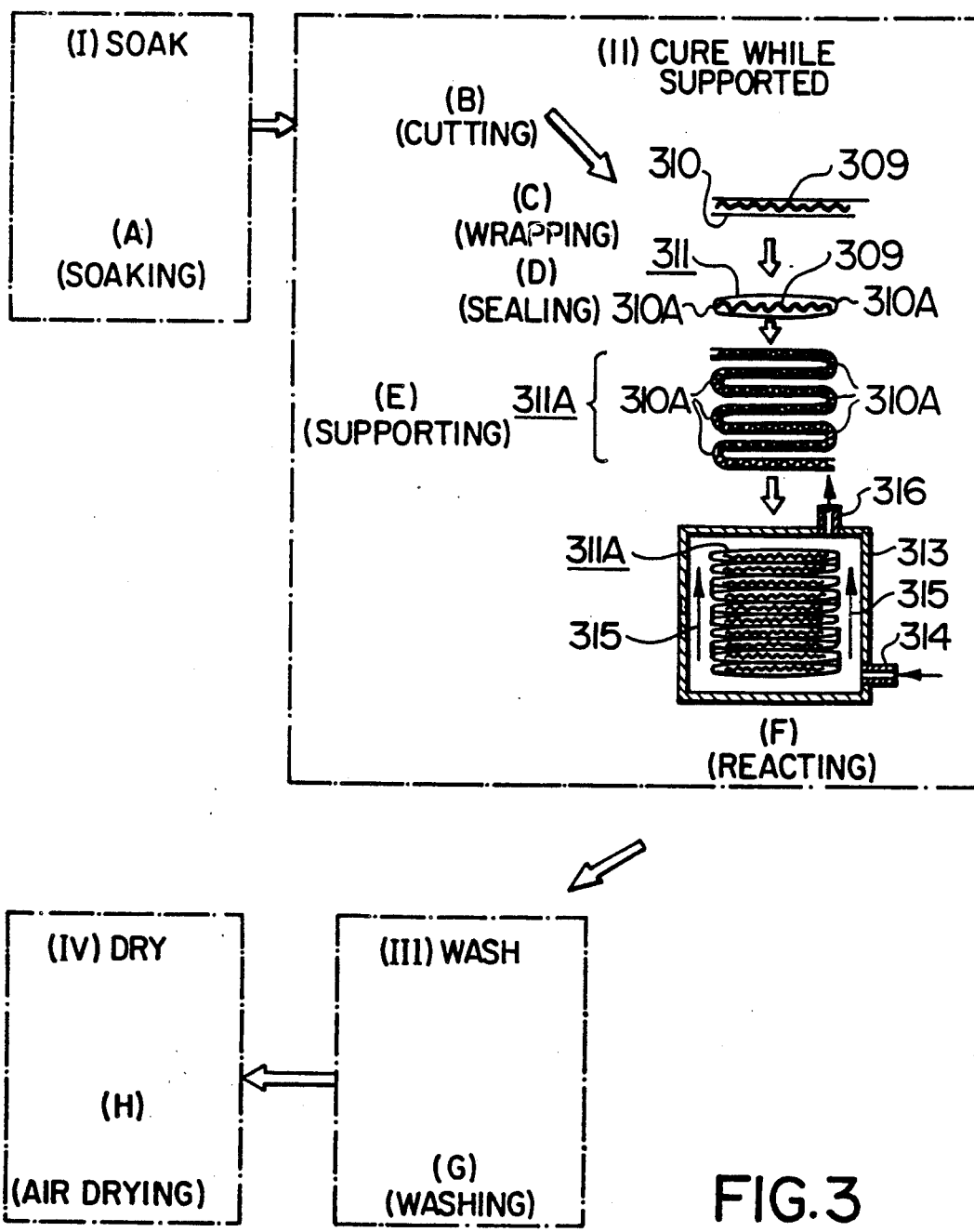
FIG. 3 is a schematic flow drawing showing another commercially-viable method using another commercially-useful system for producing another embodiment of a derivatized fabric, e.g. using a single reactant solution to provide a long length CM-cloth.

Description of FIG. 3

The first specific step depicted within block titled "(I) SATURATE" comprises process STAGE A (saturating). As seen in FIG. 3, process STAGE A (saturating) is the same as process STAGE A (saturating) which was previously described with respect to FIG. 2 and so will not be further described. This system and method is very useful for preparing long length CM-cloth using sodium monochloroacetate solution.

The second specific step depicted within block titled "(II) CURE WHILE SUPPORTED" is carried out as follows: Step (B) CUTTING was previously described with respect to FIG. 2 and so will not be further described.

At process STAGE C (wrapping), the long length of cloth 309 is placed transversely into an elongated polyethylene tube or bag 310. Then at process STAGE D (sealing), each long length of cloth 309 is sealed within tube 310, at transverse seal 310A. Then at process STAGE E, (supporting), the sealed units 311 of cloth are folded in accordion style or serpentine style to provide a stack 311A. This stage is useful for preparing CM-cloth which should not be completely dried during curing. The stack 311A is placed within a vertical air dryer 313.

At process STAGE D (reacting), a plurality of such accordion folded units 311 is placed within a vertical air dryer 313. In air dryer 313, which may be an oven which produces a hot air flow from ambient air entering via inlet 314, or which may be a drying tower fed with hot air entering via inlet 314, and in which there is efficient air circulation, the derivatization of the cloth 309 is completed by the action of the hot air. For cloths soaked with sodium monochloroacetate solution to provide CM-cloth, the cloth must not be dried at this stage. The hot air follows an upwardly-flowing path, as seen by arrows 315 and the hot air is vented by means of outlet 316. The hot air within the dryer 313 is preferably about 30° C. to about 50° C. for CM-cloth.

The third specific step depicted within block titled "(III) WASH" comprises STAGE G (washing), while the fourth specific step depicted within block titled "(IV) DRY" comprises STAGE H (drying). These are carried out as follows:

The derivatized cloth 309 is removed from the accordion-folded plastic envelope 310 and is passed to process STAGE G (washing). The washing step (G) and the air drying step (H) are the same as process STAGE E (washing), and process STAGE F (air drying), which were previously described with respect to FIG. 2, and so will not be further described.

Figure 4:
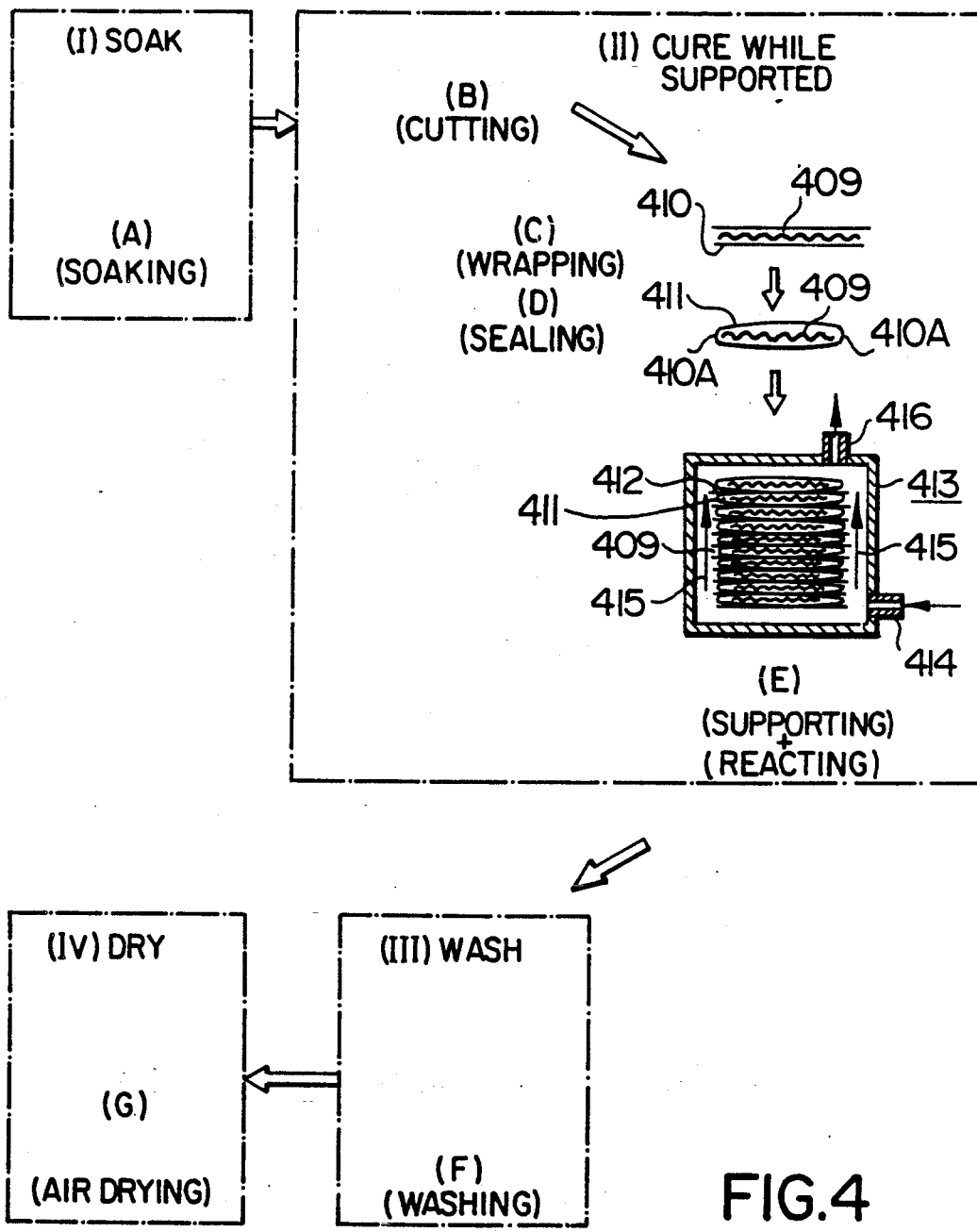
FIG. 4 is a schematic flow drawing showing another commercially-viable method using another commercially-useful system for producing another embodiment of a derivatized substrate, e.g. using a single reactant solution to provide a short length CM-cloth.

Description of FIG. 4

The first specific step depicted within block titled "(I) SATURATE" comprises process STAGE A (saturating). As seen in FIG. 3, process STAGE A (saturating) is the same as process STAGE A (saturating) which was previously described with respect to FIG. 2 and so will not be further described. This system and method is very useful for preparing short length CM-cloth using sodium monochloroacetate solution.

The second specific step depicted within block titled "(II) CURE WHILE SUPPORTED" is carried out as follows: Step (B) CUTTING was previously described with respect to FIG. 2 and so will not be further described.

At process STAGE C (wrapping), the short length of cloth 409 is placed transversely into an elongated polyethylene tube or bag 410. Then at process STAGE D (sealing), each short length of cloth 409 is sealed within tube 410 at transverse seal 410A.

Then at process STAGE E, (supporting and reacting), the sealed units 411 of cloth are stacked in directly spaced apart shelves 412 within a vertical air dryer 413. Vertical air dryer 413 may be an oven which produces a hot air flow from ambient air entering via inlet 414, or may be a drying tower fed with hot air entering via inlet 415, and in which there is efficient air circulation. The derivatization of the cloth 409 is completed by the action of the hot air. This stage is useful for preparing CM-cloth which should not be dried during curing. For cloths soaked with sodium monochloroacetate solution, to provide CM-cloth, the cloth is not dried at this stage. The hot air follows an upwardly-flowing path, as seen by arrows 415 and the hot air is vented by means of outlet 416. The hot air within the dryer 417 is preferably about 30° C. to about 50° C. for CM-cloth.

The third specific step depicted within block titled "(III) WASH" comprises STAGE G (washing), while the fourth specific step depicted within block titled "(IV) DRY" comprises STAGE H (drying). These are carried out as follows:

The derivatized cloth 409 is removed from the individual plastic envelopes 410 and is passed to process STAGE G (washing). The washing step (G) and the air drying step (H) are the same as process STAGE E (washing), and process STAGE F (air drying), which were previously described with respect to FIG. 2, and so will not be further described.

Figure 5:
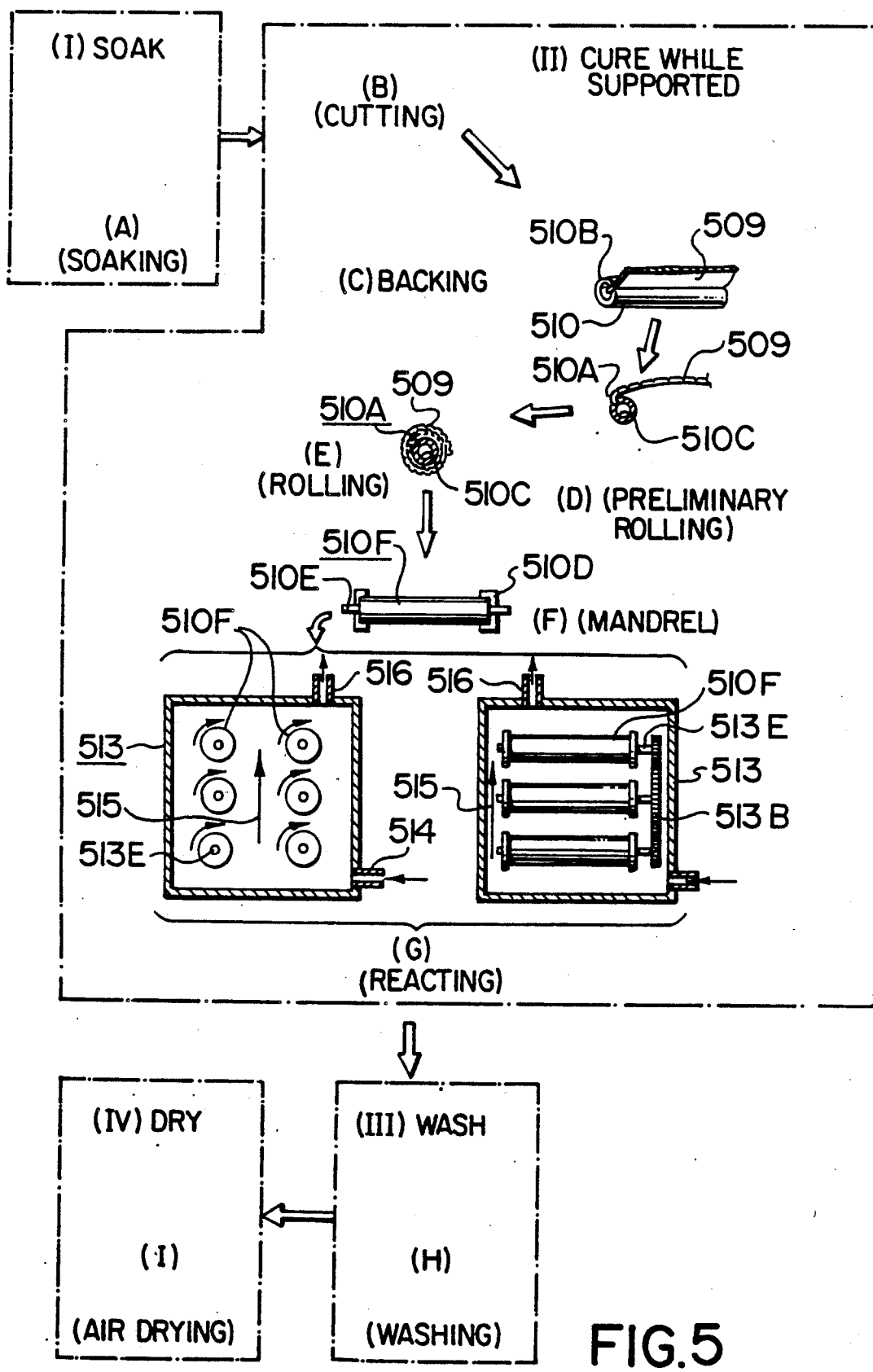
FIG. 5 is a schematic flow drawing showing another commercially-viable method using another commercially-useful system for producing another embodiment of a derivatized fabric, e.g. using a single reactant solution to provide a long length CM-cloth.

Description of FIG. 5

The first specific step depicted within block titled "(I) SATURATE" comprises the saturating step (A). As seen in FIG. 4, process STAGE A (saturating) is the same as process STAGE A (saturating), which was previously described with respect to FIG. 2, and so will not be further described. This system and method is very useful for preparing long length CM-cloth using sodium monochloroacetate solution.

The second specific step depicted within block titled "(II) CURE WHILE SUPPORTED" comprises the following steps: Step (B) CUTTING was previously described with respect to FIG. 2, and so will not be further described.

Step (C) BACKING, step (D) PRELIMINARY ROLLING, step (E) ROLLING, and step (F) MANDREL, are carried out as follows:

At process STAGE C (backing), the long size lengths of cloth 504 are backed by a long length of polyethylene sheet 510 and one end of the laminate provided thereby is placed in a slot 510A, i.e., the combined cloth 509/polyethylene sheet 510 are placed in the slot 510A in a synthetic plastic roller 510C. This stage is useful for preparing CM-cloth which should not be completely dried during curing. In process STAGE D (preliminary rolling), and process STAGE E (rolling), the combined cloth 509/polyethylene sheet 510 is first rolled to provide a rolled-up unit 510B and then in process STAGE F (mandrel), the rolled-up unit 510B is placed between a pair of respective spaced-apart roller ends 510D, each having central stub shafts 510E to provide a mandrel 510F.

At process STAGE G (reacting), which are composite mutually-transverse side and end views of a vertical air dryer 513, a plurality of such mandrels 510F containing such rolled-up units 510B is disposed so that the derivatization reaction may be completed. The mandrels 510F are placed so that they are within sub-chambers 513A which include drive means 513B to rotate the mandrels 510F mounted therein. The mandrels 510F are rotated to keep the solution in the cloth 509 homogeneous during the derivatization reaction.

The air dryer 513 may be an oven which produces a hot air flow from ambient air entering via inlet 514, or it may be a drying tower fed with hot air entering via inlet 514 and in which there is efficient air circulation. The derivatization of the cloth 509 is completed by the action of the hot air. For sodium monochloroacetate solution, to provide CM-cloth, the cloth should not be dried at this stage. The hot air follows an upwardly-flowing path, as seen by arrows 515 and the hot air along with evaporated moisture is vented by means of outlet 516. The hot air within the oven 513 is preferably 30° C. for CM-cloth.

The third specific step depicted within block titled "(III) WASH" and the fourth specific step depicted within block titled "(IV) DRY" are carried out as follows:

The derivatized cloth 509 is unwound from the support of the rollers 510C is passed to process STAGE H (washing). The washing step (H) and the air drying step (I) are the same as process STAGE E (washing), and process STAGE F (air drying), which were previously described with respect to FIG. 2, and so will not be further described.

Figure 6:
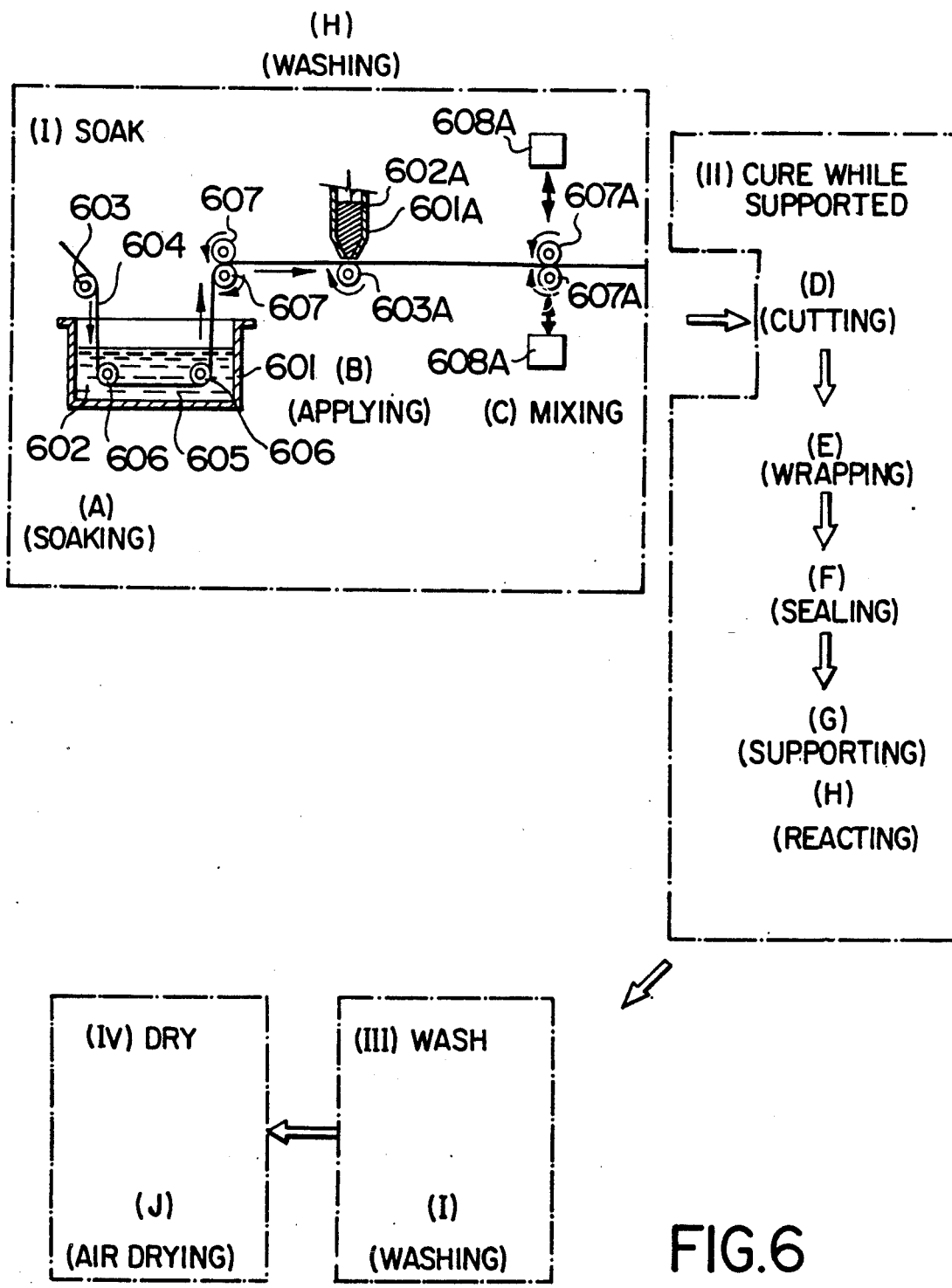
FIG. 6 is a schematic flow drawing showing another commercially-viable method using another commercially-useful system for producing another embodiment of a derivatized fabric, e.g., using a pair of reactant solutions in sequence to provide a short length DEAE-cloth.

Description of FIG. 6

The first specific step depicted within block titled "(I) SOAK" is carried out as follows: This system and method is especially useful for producing long length DEAE-cloth. As seen in FIG. 6, in process STAGE A (soaking), a container 601 is provided for a suitable solution 602, e.g., diethylaminoethyl chloride solution. Above the container 601 is an entry-guiding roller 603 for a continuously-running length of cloth 604, e.g., the SONTARA 8423 or the SONTARA 8407, as described above. The cloth 604 is caused to enter the nether regions 605 of the container 601 and is held there in reacting contact with the solution 602 by means of lower rollers 606. The cloth 604 then passed upwardly between two counter-rotating squeezing rollers 607, which are preferably adjustable to control the amount of the solution 602 in the cloth 604 and to assure that such reactant solution is uniformly adsorbed in the cloth 604.

The cloth 604, with the solution 602 uniformly-adsorbed therein, is passed to a second process STAGE B (applying), where a second reactant solution 602A, e.g. a NaOH solution saturated with $Na_2SO_4$, is placed within second applicator container 601A. The second applicator container 601A is in the form of a cylindrical container having a frusto-conical bottom outlet. Such solution is applied to cloth 604 within which the first solution was previously uniformly-adsorbed while cloth 604 is supported on roller 603A.

It is to be noted that the sodium sulfate-saturated sodium hydrochloride may be applied in the first step (saturating STAGE A), and the diethylaminoethyl chloride may be applied in the second step (saturating STAGE B) with equivalent results.

The cloth 604 then passes between two counter-rotating squeezing rollers 607A at process STAGE C, the rollers 607A preferably being adjustable to control the amount of solutions 602 and 402A in the cloth 604 and to assure that both solutions are intimately mixed and uniformly-absorbed in the cloth. To achieve this result, means, e.g., mechanism 608A and shown schematically as the double-headed arrows, are provided to result in alternate applying pressure and releasing pressure on the same region of the wetted cloth 604.

The wetted cloth 604, with the solutions 602 and 602A uniformly mixed and absorbed therein, is passed to process STAGE D (cutting) where a guillotine cutter blade 608 cuts the cloth into relatively short lengths 609.

The second specific step depicted within block titled "(II) CURE WHILE SUPPORTED" comprises the following steps: step (B) CUTTING was previously described with respect to FIG. 2, and so will not be further described.

Step (D) CUTTING, step (E) SUPPORTING and step (F) REACTING have been previously described in detail as step (B) CUTTING, step (C) SUPPORTING and step (D) REACTING with respect to FIG. 2, and so will not be further described.

The third specific step depicted within block titled "(III) WASH" and the fourth specific step depicted within block titled "(IV) DRY" are carried out as follows:

The derivatized cloth is removed from the support of the plates and is passed to process STAGE E (washing).

The washing step (H) and the air drying step (I) are the same as process STAGE E (washing), and process STAGE F (air drying), which were previously described with respect to FIG. 2, and so will not be further described.

Figure 7:
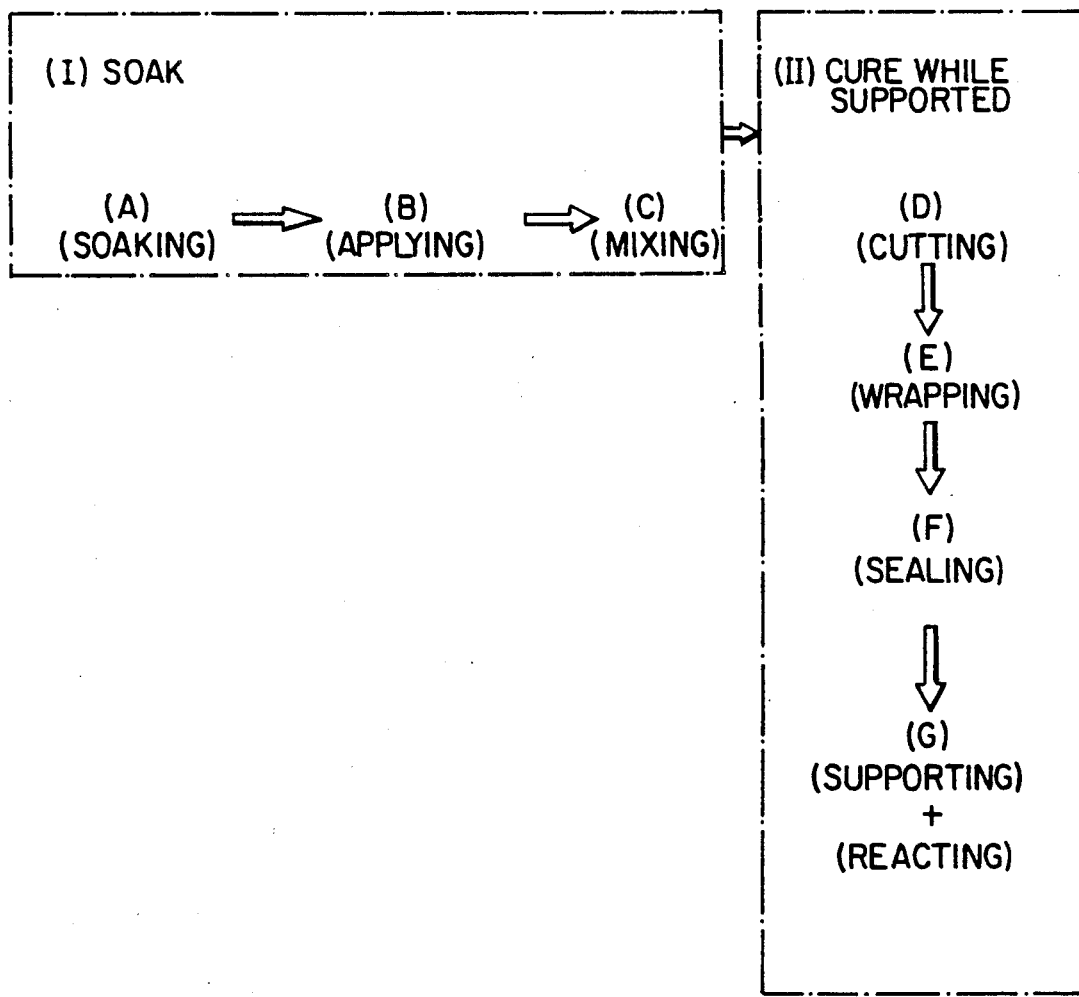
FIG. 7 is a schematic flow drawing showing another commercially-viable method using another commercially-useful system for producing another embodiment of a derivatized substrate, e.g., using a pair of reactant solutions in sequence to provide a short length DEAE-cloth.

Description of FIG. 7

The first specific step depicted within block titled "(I) SOAK" is carried out as follows: This method and system is especially useful for producing short length DEAE-cloth. As seen in FIG. 7, the soaking step (A), the applying step (B), and the mixing step (C), are the same as process STAGE A (soaking), process STAGE B (applying), and process STAGE C (mixing), which were previously described with respect to FIG. 6, and so will not be further described.

The second specific step depicted within block titled "(III) CURE WHILE SUPPORTED" is carried out as follows: Step (D) CUTTING was previously described with respect to FIG. 2, and so will not be further described. Step (E) WRAPPING, step (F) SEALING, step (G) SUPPORTING and step (H) REACTING, are the same as process STAGE C (wrapping), process STAGE D (sealing), process STAGE E (supporting), and process STAGE F (reacting), which were previously described with respect to FIG. 3, and so will not be further described.

The third specific step depicted within block titled "(III) WASH" and the fourth specific step depicted within block titled "(IV) DRY" are carried out as follows:

The derivatized cloth is removed from the plastic envelopes and is passed to process STAGE G (washing). The washing step (H) and the air drying step (I) are the same as process STAGE E (washing), and process STAGE F (air drying), were previously described with respect to FIG. 2, and so will not be further described.

Figure 8:
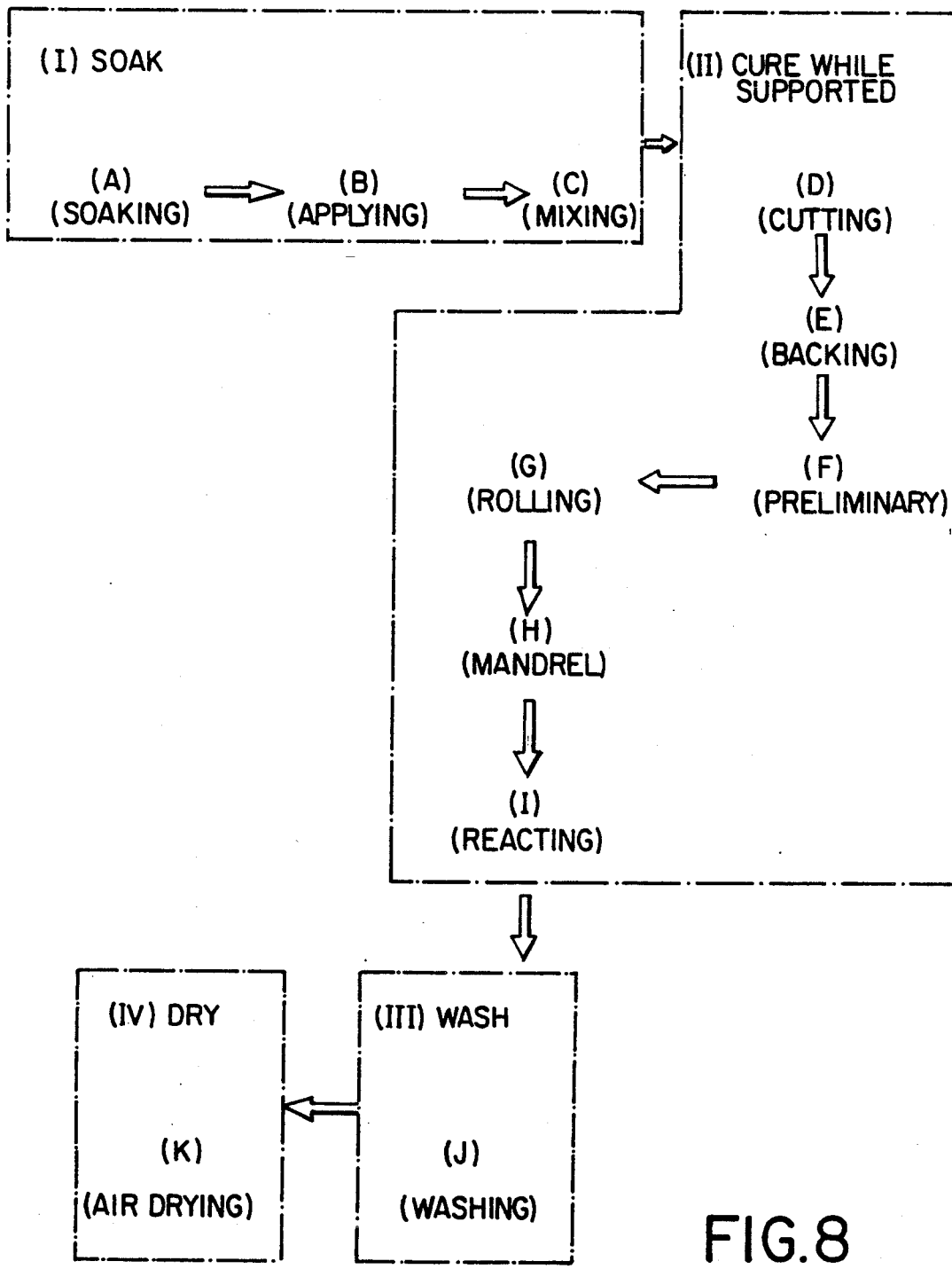
FIG. 8 is a schematic flow drawing showing another commercially-viable method using another commercially-useful system for producing another embodiment of a derivatized fabric, e.g. using a pair of reactant solutions in sequence to provide a long length DEAE-cloth.

Description of FIG. 8

The first step depicted within block titled "(I) SOAK" is carried out as follows: This method and system is especially useful for producing long length DEAE-cloth. As seen in FIG. 8, the soaking step (A), the applying step (B), and the mixing step (C) are the same as process STAGE A (soaking), process STAGE B (applying), and process STAGE C (mixing), which were previously described with respect to FIG. 5, and so will not be described further.

The second specific step depicted within block titled "(II) CURE WHILE SUPPORTED" is carried out as follows: Step (D) CUTTING was previously described with respect to FIG. 2, and so will not be further described. Backing step (E), preliminary rolling step (F), rolling step (G), mandrel step (H), and reacting step (I), are the same as process STAGE C (backing), process STAGE D (preliminary rolling), process STAGE E (rolling), process STAGE F (mandrel), and process STAGE G (reacting), were previously described with respect to FIG. 5, and so will not be described further.

The third specific step depicted within block titled "(III) WASH" and the fourth specific step depicted within block titled "(IV) DRY" are carried out as follows: The derivatized cloth is unwound from the support of the rollers and is passed to process STAGE J (washing). Washing step (J) and air drying step (K) are the same as process STAGE E (washing), and process STAGE F (air drying), which were previously described with respect to FIG. 2, and so will not be described further.

Figure 9:
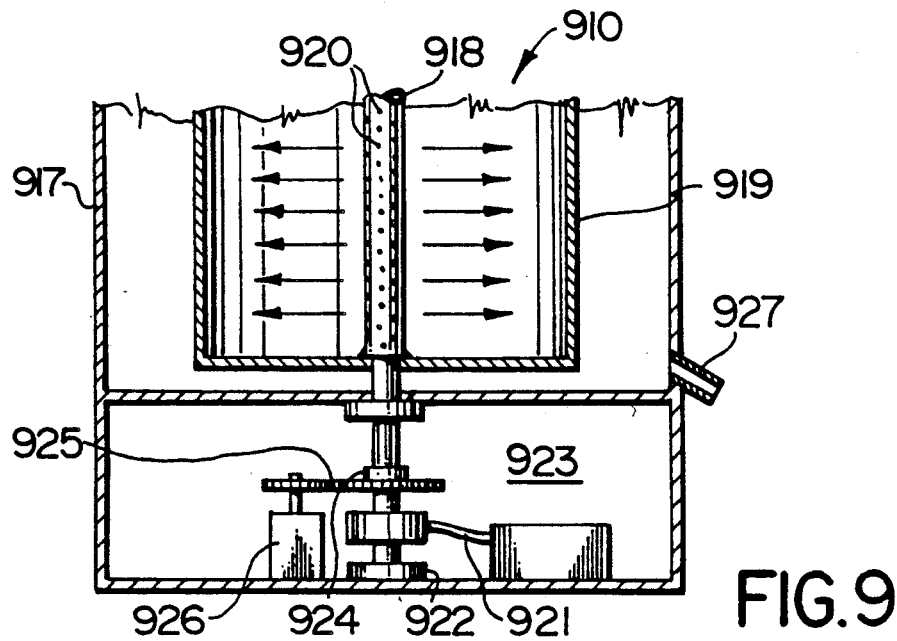
FIG. 9 is a schematic vertical sectional view of one form of a centrifugal washer used in the method of embodiments of the present invention.

Description of FIG. 9

As seen in FIG. 9, the centrifugal washer 910 includes a cylindrical casing 917 containing a perforated basket 919 concentrically mounted therein around, and fixedly secured to a central hollow shaft 918. The central shaft 918 is provided with a plurality of apertures 920, arrayed not only around the circumference of shaft 918, but also along its longitudinal (vertical) length. The washing solution, may be any solution as previously described. However, the washing with $H_2O$ enters the hollow shaft 918 through inlet line 921. Shaft 918 is mounted for rotation on a bushing 922 and meshes by its driven gear 923 to a drive gear 924 on drive shaft 925 of motor 926. The shaft 918 is also connected to basket 919 so that the basket 919 may be rotated centrifugally along with the shaft 918.

The wash solution which escapes through the apertures in basket 919 is drained away through drain 927.

Operation of Preferred Embodiments

The following are examples of the methods of embodiments of this invention, using the system of this invention.

EXAMPLE 1

Preparation of $SO_3$-Cloth

The apparatus shown in FIG. 2 is used in this Example.

In the first step, the cloth is immersed in a sulfamic acid-urea bath to produce a $SO_3$-cloth and is picked up to proceed to a roller squeezer which controls the amount of the solution on the cloth. The cloth is then cut to a suitable short-length size. The roller squeezers should be adjustable to squeeze at a selected pressure to give a better capillary absorption effect, in order to assure that the solution is uniformly-absorbed within the cloth.

In the second step, the cloth is cut to short lengths.

In the third step, the cut cloth is placed flat on a glass or plastic plate. It is preferred that both ends of the cloth be strapped to the plate. Alternatively, short cut lengths of cloth may be piled one atop another by being sandwiched between separate polyethylene sheets.

In the fourth step, the cloth, which is strapped onto the plate, is slid into av oven which can gently and efficiently circulate hot air, at 100° C. for $SO_3$-cloth, substantially completely to dry the cloth and to carry away moisture. The cloth is substantially completely dried during the course of this curing reaction.

In the fifth step, the cloth from the dryer is placed in a washer (e.g. as shown in FIG. 9) which can spray water and/or chemical treating solution from a rotating central hollow shaft, onto a rotating basket which holds the cloth.

In the sixth step, after such centrifuging, the well-washed cloth is then dried, preferably air-dried.

EXAMPLE 2

Preparation of CM-cloth

The apparatus shown in FIG. 3 is used in this Example.

For the preparation of CM-cloth, in the first step, the cloth is soaked in a sodium monochloroacetate bath. The cloth is taken up by counter-rotating rollers to squeeze out excess solution and also to control the amount of such reactant solution. The squeezing should be adjustable to squeeze at a selected pressure to give a better capillary absorption effect in order to assure that the solution is uniformly-absorbed within the cloth.

In the second step, the cloth is cut into long lengths.

In the third step, the long cut lengths of cloth are encased in a long polyethylene bag or long polyethylene tube and sealed at both ends of the long length of cloth.

In the fourth step, the sealed short lengths of cloth are folded into an accordian or serpentine configuration at the seal.

In the fifth step, the accordian-folded encased cloths are placed within a 30° C. environment (e.g. a chamber or oven with efficient air circulation to carry away moisture). The cloth is partially dried during the course of this curing reaction.

In the sixth step, the cloth from the dryer is placed in a washer (e.g. as shown in FIG. 9) which can spray water and/or chemical treating solution from a rotating central hollow shaft, onto a rotating basket which holds the cloth.

After such centrifuging, in the sixth step, the well-washed cloth is then dried, preferably air-dried.

EXAMPLE 3

Preparation of CM-cloth

The apparatus shown in FIG. 4 is used in this Example.

For the preparation of CM-cloth, in the first step, the cloth is soaked in a sodium monochloroacetate bath. The cloth is taken up to counter-rotating rollers to squeeze out excess solution and also to control the amount of reactant solution and to assure that such reactant solution is uniformly absorbed in the cloth. The squeezing should be adjustable to squeeze at a selected pressure to give a better capillary effect in order to assure that the solution is uniformly-absorbed within the cloth.

In the second step, the cloth is cut into short lengths.

In the third step, each individual length of the short cut lengths of cloth is encased in its own polyethylene bag or polyethylene tube which is then sealed at both ends.

In the fourth step, the sealed short lengths of cloth are folded into an accordian or serpentine configuration.

In the fifth step, the accordian folded encased cloths are placed on spaced-apart shelves 412 within a 30° C. environment (e.g. a chamber or oven with efficient air circulation to carry away moisture). The cloth is partially dried during the course of this curing reaction.

In the sixth step, the cloth from the dryer is placed in a washer (e.g. as shown in FIG. 9) which can spray water and/or chemical treating solution, e.g., 0.5N NaOH, from a rotating central hollow shaft, onto a rotating basket which holds the cloth.

After such centrifuging, in the sixth step, the well-washed cloth is then dried, preferably air-dried.

EXAMPLE 4

Preparation of CM-Cloth

The apparatus shown in FIG. 5 is used in this Example.

For the preparation of CM-cloth, in the first step, the cloth is soaked in a sodium monochloroacetate bath. The cloth is taken up to counter-rotating rollers to squeeze out excess solution and also to control the amount of reactant solution and to assure that such reactant solution is uniformly absorbed in the cloth. The squeezing should be adjustable to squeeze at a selected pressure to give a better capillary effect in order to assure that the solution is uniformly-absorbed within the cloth.

In the second step, the cloth is cut into long lengths and is sealed in a polyethylene sheet, or in a bag or tube (e.g. that known by the Trade Mark POLYPHAME by Ralstone Research, flat width 75 cm). The cloth is snap fixed at one end to a cylinder together with a polyethylene sheet placed underneath the cut cloth, the polyethylene sheet being slightly larger than the size of the cloth, and is rolled around the cylinder. The end of the roll is sealed and both sides of the cylinder are capped by plastic caps.

In the third step, the cylinders are connected to rods connected to gears arranged for slow turning, to prevent the solution from draining down, in a 30° C. chamber or oven in which there is efficient air circulation.

In the fourth step, the CM-cloth is placed in a centrifugal washer (e.g. as shown in FIG. 9) which is provided with a hollow shaft to spray water (or preferably aqueous alcohol to remove organic reagents thoroughly) to wash away the reagent while the cloths which are hung on a rotating basket are centrifuging. The hollow shaft is also capable of spraying chemical treating solution, e.g., 0.5N NaOH for activation of the cloth.

In the fifth step, the well-washed cloths are then dried, preferably air-dried.

EXAMPLE 5

Preparation of DEAE-cloth

The apparatus shown in FIG. 6 is used in this Example.

For the preparation of DEAE-cloth, in the first step, the cloth is soaked either in a first solution of diethylaminoethyl chloride bath, or in a first solution of sodium sulfate-saturated sodium hydroxide bath. The cloth is taken up by counter-rotating rollers to squeeze out excess solution and also to control the amount of such reactant solution. The squeezing should be adjustable to squeeze at a selected pressure to give a better capillary absorption effect and to assure that such reactant solution is uniformly absorbed in the cloth.

In the second step, either a second solution of sodium sulfate-saturated sodium hydroxide solution, or in a second solution of a diethlaminoethyl chloride bath, respectively, is applied in a controlled amount and the cloth is passed through a second set of counter-rotating rollers to assure even distribution and mixing of both reagents and to assure that both solutions are intimately mixed and uniformly-absorbed in the cloth.

The sodium sulfate-saturated sodium hydroxide may be applied as the first solution in the first step, and the diethylaminoethyl chloride may be applied as the second solution in the second step with equivalent results.

In the third step, the cloth is then cut into suitable long lengths.

In the fourth step, the cloth is cut into long lengths and is sealed in a polyethylene sheet, or in a bag or tube (e.g. that known by the Trade Mark POLYPHAME by Ralstone Research, flat width 75 cm). The cloth is snap fixed at one end to a cylinder together with a polyethylene sheet placed underneath the cut cloth, the polyethylene sheet being slightly larger than the size of the cloth, and is rolled around the cylinder. The end of the roll is sealed and both sides of the cylinder are capped by plastic caps.

In the fifth step, the cylinders are connected to rods connected to gears arranged for slow turning, to prevent the solution from draining down, in a 30° C. chamber or oven in which there is efficient air circulation.

In the sixth step, the derivatized cloth is placed in a centrifugal washer (e.g. as shown in FIG. 9) which sprays water (or preferably aqueous alcohol, thoroughly to remove organic reagents) to wash away the reagent from a rotating hollow shaft while the cloth is hung on a basket which is rotating along with the rotating hollow shaft. The hollow shaft is also capable of spraying a chemical treating solution, e.g., 0.5N. HCl for activation of the cloth.

In the seventh step the well-washed cloths are then dried, preferably air-dried.

EXAMPLE 6

Preparation of DEAE-cloth

The apparatus shown in FIG. 7 is used in this Example.

For the preparation of DEAE-cloth, in the first step, the cloth is soaked either in a diethylaminoethyl chloride bath or in a sodium sulfate-saturated sodium hydroxide bath. The cloth is taken up by counter-rotating rollers to squeeze out excess solution and also to control the amount of such reactant solution and to assure that such reactant solution is uniformly absorbed in the cloth. The squeezing rollers should be adjustable to squeeze at a selected pressure to give a better capillary absorption effect in order to assure that the solution is uniformly-absorbed within the cloth.

In the second step, either a sodium sulfate-saturated sodium hydroxide solution or a diethylaminoethyl chloride solution, respectively, is applied in a controlled amount and the cloth is passed through a second set of counter-rotating rollers to assure even distribution and mixing of both reagents. To achieve this result, means are provided to result in alternate applying pressure and releasing pressure on the same region of the cloth.

The sodium sulfate-saturated sodium hydroxide may be applied as the first solution in the first step, and the diethylaminoethylchloride may be applied (as the second solution) in the second step with equivalent results.

In the third step, the cloth is then cut to a suitable short length.

In the fourth step, each individual short cut length of cloth is encased in a polyethylene bag or tube, which is sealed at both ends. The short lengths of cut cloth may alternatively be piled one atop the other by being sandwiched between polyethylene sheets.

In the fifth step, the encased cloths are piled one atop another or placed on shelves in a 30° C. environment (e.g. a chamber or oven) to cure, while there is efficient air circulation.

In the sixth step, the derivatized cloth is placed in a centrifugal washer (e.g. as shown in FIG. 9) which sprays water (or preferably aqueous alcohol, thoroughly to remove organic reagents) to wash away the reagent from a rotating hollow shaft while the cloth is hung on a basket which is rotating along with the rotating hollow shaft. The hollow shaft is also capable of spraying a chemical treating solution, e.g., 0.5N. HCl for activation of the cloth.

In the seventh step the well-washed cloths are then dried, preferably air-dried.

EXAMPLE 7

Preparation of DEAE-Cloth

The apparatus shown in FIG. 8 is used in this Example.

For the preparation of DEAE-cloth, in the first step, the cloth is soaked either in a first solution of diethylaminoethyl chloride bath, or in a first solution of sodium sulfate-saturated sodium hydroxide bath. The cloth is taken up by counter-rotating rollers to squeeze out excess solution and also to control the amount of such reactant solution. The squeezing should be adjustable to squeeze at a selected pressure to give a better capillary absorption effect and to assure that such reactant solution is uniformly absorbed in the cloth.

In the second step, either a second solution of sodium sulfate-saturated sodium hydroxide solution, or in a second solution of a diethlaminoethyl chloride bath, respectively, is applied in a controlled amount and the cloth is passed through a second set of counter-rotating rollers to assure even distribution and mixing of both reagents and to assure that both solutions are intimately mixed and uniformly-absorbed in the cloth.

The sodium sulfate-saturated sodium hydroxide may be applied as the first solution in the first step, and the diethylaminoethyl chloride may be applied as the second solution in the second step with equivalent results.

In the third step, the cloth is then cut into suitable long lengths.

In the fourth step, the soaked long lengths of cloth are sealed in a polyethylene sheet, or bag or tube (e.g., that known by the Trade Mark POLYPHAME by Ralstone Research, flat width 75 cm). The cloth is snap fixed at one end to a cylinder together with a polyethylene sheet placed underneath the long lengths of cut cloth, the size of the polyethylene sheet being slightly larger than the size of the cloth. The combination is rolled around the cylinder. The end of the roll is sealed and both ends of the cylinder are capped by plastic caps.

In the fifth step, the cylinders are connected to rods connected to gears, arranged for slow turning to prevent the solution from draining down, in a 30° C. chamber or oven with efficient air circulation.

In the sixth step, the cloth is placed in a centrifugal washer (e.g. that shown in FIG. 9) which sprays water from a rotating hollow shaft (or preferably aqueous alcohol thoroughly to remove organic reagents) to wash away the reagent while the cloth which is hung in a basket which is rotating along with the hollow shaft. The hollow shaft is also capable of spraying a chemical treating solution, e.g., 0.5N HCl for activation of the DEAE-cloth.

In the seventh step, the well-washed cloths are then dried, preferably air-dried.

CONCLUSION

This invention provides commercially-viable methods and commercially-useful systems for preparing derivatized cellulose cloths or fabrics. The methods and systems make it possible to provide commercial-scale amounts of products, rather than laboratory-scale amounts of derivatized cloths, as in the prior art.

Industrial plants can thus prepare a wound or burn dressing according to the methods and systems of this invention which provide commercially-viable methods for producing derivatized cloths. Subsequently, an ionic form of a physiologically- or biologically-active substance can be adsorbed and bound thereto, to provide a wound dressing. Upon contact with body exudate from wounds or burns to which such wound dressing is applied, the physiologically- or biologically-active substance is released by ion exchange with ions in the exudate, in tempo with the release of such ions and in tempo with the production of exudate. This controlled release thus reduces unnecessary exposure of undamaged tissue to the physiologically- or biologically-active substance.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly equitably, and "intended" to be, within the full range of equivalence of the following claims.

We claim:

1. A wound dressing for systemic administration of a physiologically- or biologically-active agent by controlled release of the agent into such wound, said wound dressing comprising:
   (a) a substrate in the form of a fabric or cloth, at least a portion of which is cellulosic, which has been chemically modified to convert hydroxyl groups in said cellulosic portion to ionic-adsorbing sites;
   (b) an ionic form of a physiologically- or biologically-active agent adsorbed in said substrate, said agent being selected from the group consisting of anti-bacterial agents, antifungal agents, analgesic agents, tissue healant agents, local anesthetic agents, antibleeding agents, enzymers and vasoconstrictors; and
   (c) ionic bonds holding said agent temporarily to said substrate for controlled release therefrom in proportion to the amount of exudate in contact with the substrate, said ionic bonds being formed by adsorbing said agent on said substrate at room temperature, said ionic bonds disassociating upon contact with body exudate from wounds to which said wound dressing is applied by ion exchange with ions in the body exudate, thereby to release said physiologically- or biologically-active agent in an amount in proportion to the amount of said exudate in contact with the substrate.

2. The wound dressing of claim 1 wherein said substrate is a dialkylaminoalkyl cloth.

3. The wound dressing of claim 2 wherein said substrate is a diethylaminoethyl cloth, a diethylaminomethyl cloth, a dimethylaminoethyl cloth, or a dimethylaminopropyl cloth.

4. The wound dressing of claim 2 wherein said substrate is diethylaminoethyl cloth.

5. The wound dressing of claim 1 wherein said substrate is a carboxyalkyl cloth.

6. The wound dressing of claim 5 wherein said substrate is a carboxymethyl cloth, a carboxyethyl cloth or a carboxypropyl cloth.

7. The wound dressing of claim 6 wherein said substrate is a carboxymethyl cloth.

8. The wound dressing of claim 1 wherein said substrate is an $SO_3$-cloth

9. The wound dressing of claim 1 wherein said physiologically- or biologically-active agent is in the form of its salt.

10. The wound dressing of claim 4 wherein said physiologically- or biologically-active agent is an anionic antifungal.

11. The wound dressing of claim 10 wherein said physiologically- or biologically-active agent anionic antifungal is selected from the group consisting of nafcillin, nystatin, and undecylenic acid, and salts thereof.

12. The wound dressing of claim 4 wherein said physiologically- or biologically-active agent is an anionic analgesic.

13. The wound dressing of claim 12 wherein said anionic analgesic is selected from the group consisting of salicylic acid, salicylsulfonic acid and nicotinic acid, and salts thereof.

14. The wound dressing of claim 4 wherein said physiologically- or biologically-active agent is an antibleeding agent comprising adenosine diphosphate.

15. The wound dressing of claim 7 wherein said physiologically- or biologically-active agent is a cationic anti-bacterial.

16. The wound dressing of claim 15 wherein said cationic anti-bacterial is selected from the group consisting of chlorhexidine, bacitracin, chlortetracycline, gentamycin, kanamycin, neomycin B, polymyxin B, streptomycin, and tetracycline, and salts thereof.

17. The wound dressing of claim 7 wherein said physiologically- or biologically-active agent is a cationic antifungal.

18. The wound dressing of claim 17 wherein said cationic anti-fungal is selected from the group consisting of amphotericin B, clotrimazole, and miconazole, and salts thereof.

19. The wound dressing of claim 7 wherein said physiologically- or biologically-active agent is a cationic tissue healant.

20. The wound dressing of claim 19 wherein said cationic tissue healant is selected from the group consisting of cysteine, glycine and threonine, and salts thereof.

21. The wound dressing of claim 7 wherein said physiologically- or biologically-active agent is a cationic local anesthetics selected from the group consisting of lidocaine, and salts thereof.

22. The wound dressing of claim 7 wherein said physiologically- or biologically-active agent is a cationic enzyme.

23. The wound dressing of claim 22 wherein said cationic enzyme is selected from the group consisting of trypsin, streptokinase, plasmin and streptodornase, and salts thereof.

24. The wound dressing of claim 7 wherein said physiologically- or biologically-active agent is deoxyribonuclease.

25. The wound dressing of claim 7 wherein said physiologically- or biologically-active agent is a cationic vasoconstrictor.

26. The wound dressing of claim 25 wherein said cationic vasoconstrictor is selected from the group consisting of epinephrine and serotonin.

27. The wound dressing of claim 8 wherein said physiologically- or biologically-active substance is a cationic anti-fungal.

28. The wound dressing of claim 27 wherein said cationic antifungal is selected from the group consisting of amphotericin B, clotrimazole, and miconazole, and salts thereof.

29. The wound dressing of claim 8 wherein said physiologically- or biologically-active substance is a cationic tissue healant.

30. The wound dressing of claim 29 wherein said cationic tissue healant, is selected from the group consisting of cysteine, glycine and threonine, and salts thereof.

31. The wound dressing of claim 8 wherein said physiologically- or biologically-active substance is a cationic antibacterial.

32. The wound dressing of claim 31 wherein said cationic antibacterial is selected from the group consisting of chlorohexidine, bacitracin, chlortetracycline, gentamycin, kanamycin, neomycin B, polymyxin B, streptomycin and tetracycline, and salts thereof.

33. The wound dressing of claim 32 wherein said local anaesthetic is selected from the group consisting of lidocaine, and salts thereof.

34. The wound dressing of claim 8 wherein said physiologically- or biologically-active substance is a cationic enzyme.

35. The wound of claim 34 wherein said cationic enzymer is selected from the group consisting of trypsin, streptokinase, plasmin and streptodornase, and salts thereof.

36. The wound dressing of claim 8 wherein said physiologically- or biologically-active substance is deoxyribonuclease.

37. The wound dressing of claim 8 wherein said physiologically- or biologically-active substance is a cationic vasoconstrictor.

38. The wound dressing of claim 37 wherein said cationic vasoconstrictor is selected from the group consisting of epinephrine and serotonin.

39. The wound dressing of claim 8 wherein said physiologically- or biologically-active substance is chlorohexidine digluconate.

40. The wound dressing of claim 1 wherein said substrate is a fabric.

41. The wound dressing of claim 40 wherein said fabric is a non-woven rayon fabric or a non-woven rayon/polyester cloth.

42. The wound dressing of claim 41 wherein said fabric is in the form of an open-apertures style, or in the form of a highly absorbent, open-apertures style.

* * * * *